(12) United States Patent
Pandya

(10) Patent No.: US 8,361,079 B2
(45) Date of Patent: Jan. 29, 2013

(54) METHOD FOR DRILLING ENLARGED SECTIONS OF ANGLED OSTEAL TUNNELS

(76) Inventor: Rajiv D. Pandya, Atlanta, GA (US)

( * ) Notice: Subject to any disclaimer, the term of this patent is extended or adjusted under 35 U.S.C. 154(b) by 192 days.

(21) Appl. No.: 12/705,686

(22) Filed: Feb. 15, 2010

(65) Prior Publication Data

US 2010/0228254 A1  Sep. 9, 2010

Related U.S. Application Data

(63) Continuation-in-part of application No. 12/270,506, filed on Nov. 13, 2008, and a continuation-in-part of application No. 12/270,492, filed on Nov. 13, 2008, and a continuation-in-part of application No. 12/270,513, filed on Nov. 13, 2008, and a continuation-in-part of application No. 12/270,525, filed on Nov. 13, 2008.

(51) Int. Cl.
*A61B 17/00* (2006.01)
(52) U.S. Cl. ............................. 606/96; 606/80; 606/98
(58) Field of Classification Search ............ 623/13.12, 623/13.14; 606/80, 86 R, 96, 98, 148
See application file for complete search history.

(56) References Cited

U.S. PATENT DOCUMENTS

| | | | | |
|---|---|---|---|---|
| 5,688,284 | A * | 11/1997 | Chervitz et al. | 606/96 |
| 2003/0065391 | A1 * | 4/2003 | Re et al. | 623/13.14 |
| 2004/0092936 | A1 * | 5/2004 | Miller et al. | 606/72 |
| 2006/0241657 | A1 * | 10/2006 | Cerundolo | 606/148 |
| 2007/0233151 | A1 * | 10/2007 | Chudik | 606/96 |
| 2007/0250067 | A1 * | 10/2007 | Schmieding et al. | 606/96 |

\* cited by examiner

*Primary Examiner* — Kevin T Truong
*Assistant Examiner* — Christian Sevilla
(74) *Attorney, Agent, or Firm* — David L King

(57) ABSTRACT

Methods for drilling enlarged osteal tunnels using osteal guides capable of drilling an angled osteal tunnel, namely, an osteal tunnel having an angle or turn within the bone and for drawing a muscle, tendon or ligament in need of repair into the enlarged osteal tunnel such that the bone can mend about, around, over and/or within the muscle, tendon or ligament. A reamer and guide wire can be used to create the enlarged osteal tunnel to accommodate a portion of the muscle, tendon or ligament in need of repair. The device allows for the blind intraosseous preparation of osteal tunnels and the blind intraosseous retrieval of sutures from such osteal tunnels.

16 Claims, 13 Drawing Sheets

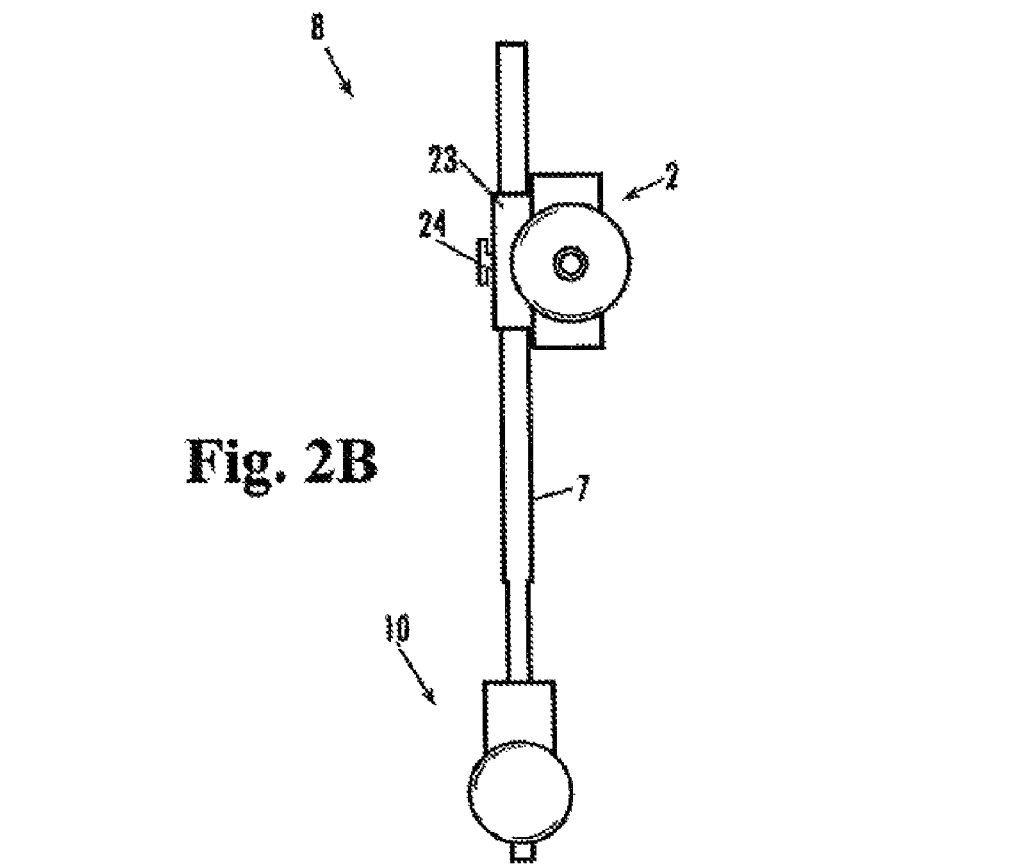
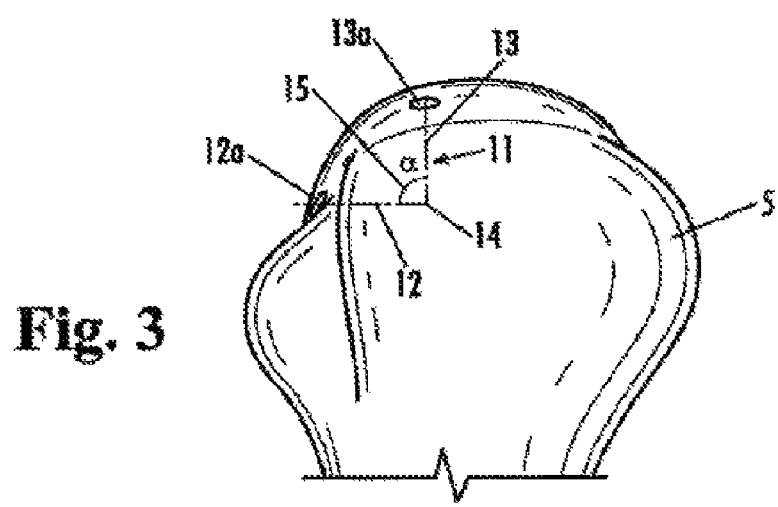

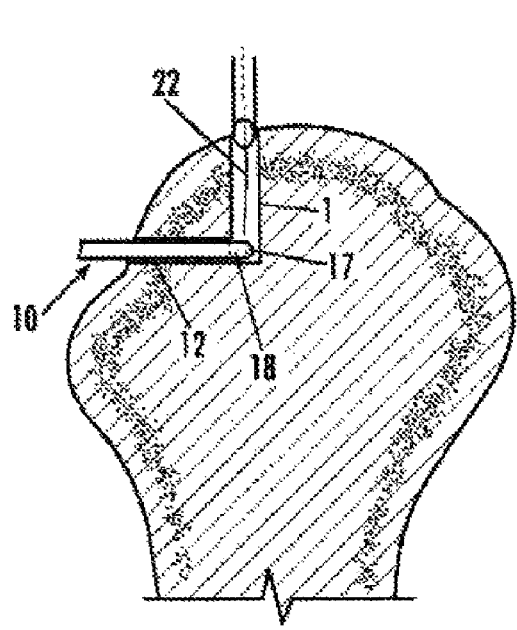
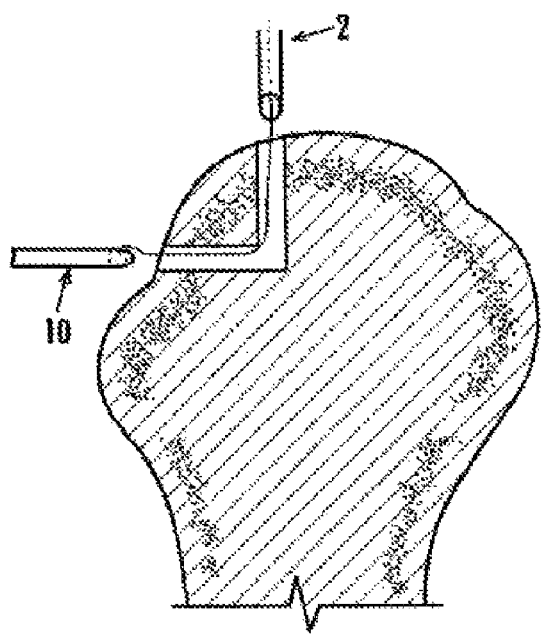
Fig. 5     Fig. 6
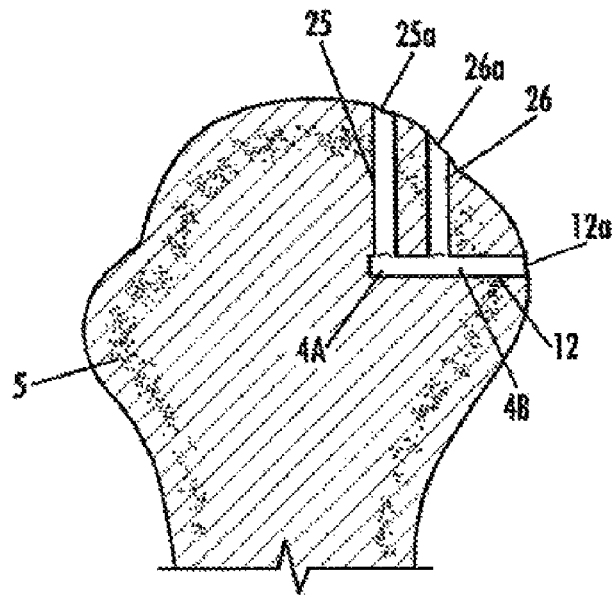
Fig. 7

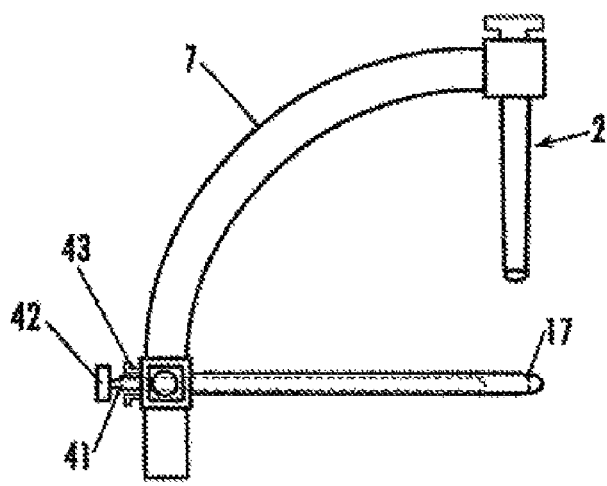
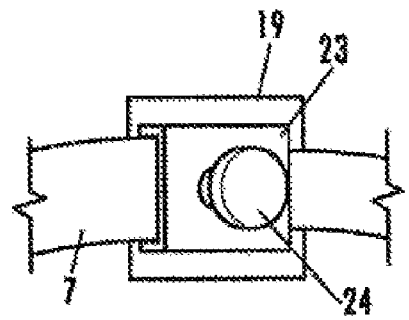
Fig. 16
Fig. 18A
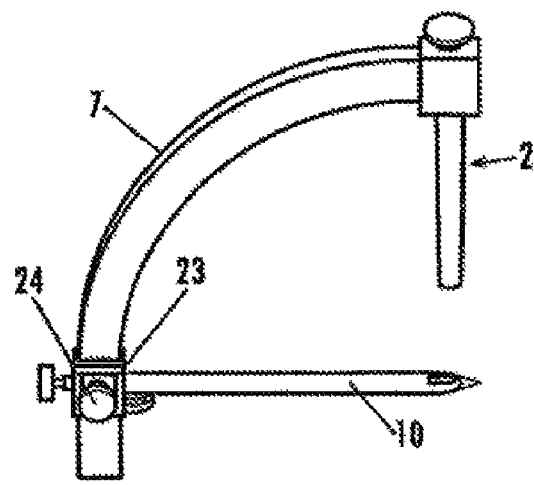
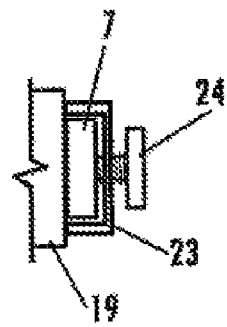
Fig. 17
Fig. 18B

METHOD FOR DRILLING ENLARGED SECTIONS OF ANGLED OSTEAL TUNNELS

STATEMENT OF RELATED APPLICATIONS

This application is a continuation-in-part of copending U.S. patent application Ser. No. 12/270,506 filed Nov. 13, 2008, U.S. patent application Ser. No. 12/270,492 filed Nov. 13, 2008, U.S. patent application Ser. No. 12/270,513 filed Nov. 13, 2008, and U.S. patent application Ser. No. 12/270,525 filed Nov. 13, 2008.

BACKGROUND OF THE INVENTION

1. Technical Field

The present invention generally is related to the field of osteal guides, surgical drilling systems and methods for drilling osteal tunnels, and more particularly is related to the creation of enlarged sections in angled osteal tunnels for anchoring ligament, muscle and tendon segments.

2. Related Art

The anterior and posterior cruciate ligaments in the knee assist in providing stability to the function of the knee. The cruciate ligaments control gliding, sliding, and rotation of the knee. To accomplish this, the anterior and posterior cruciate ligaments function according to the principles of a crossed four bar linkage, which is closely related to and dependent upon the bony constraints of the surrounding bones. Thus, the anatomic origin and insertion of both of the ligaments is crucial. Often the anterior cruciate ligament (ACL) becomes ruptured or torn, requiring replacement and reconstruction of the ligament in order to restore normal usage of the knee. When the ACL is restored or replaced, the ACL or a substitute synthetic or harvested graft must be reattached to the bone. The ACL graft is anchored in place either inside or outside of osteal tunnels or passages formed in the tibia or femur. It is preferential to locate and drill the tunnels at precise locations so the ACL will be reattached at the natural location or so the graft will be implanted in the optimum position. If a ligament reconstruction is performed in the appropriate location, then normal motion and stability can be restored. Otherwise, the ligament will eventually be too loose or too tight for normal function.

Similarly, tissue repair to the shoulder area, such as reattaching torn rotator cuff tendons to bone, also can be accomplished through open surgery or arthroscopic surgery. Because open surgery introduces potential problems with the trauma associated with the large area of skin, muscle and tissue that must be incised to perform such surgery, arthroscopic surgery is preferred because it has the advantages of requiring only a small incision, thus reducing the risk of infection, blood loss and the like sometimes caused by open surgery. The rotator cuff can be reattached to the humerus by suturing the tendon to the bone by passing the suture through a transosteal tunnel drilled through the proximal portion of the humerus. The location at which the tunnel is to be drilled is paramount because the axillary nerve, a major nerve which innervates the deltoid muscle, lies close to the preferred reattachment site. Movement of the shoulder may be impaired if the axillary nerve is damaged. Often, this results in a tunnel being close to the surface of the bone, which tunnel may have a thin wall and therefore be relatively weak and subject to breaking.

The repair of torn ligaments by anchoring them into an osteal tunnel created within the affected bone is dependent upon complex interdependencies between the ligaments of a human body. Not only must an osteal tunnel be created so as to provide optimal positioning and tension, but avoidance of major nerves, blood vessels, and other anatomical obstructions also dictate the positioning of the tunnels. Further, while it may be desirable for surgeons to employ their discretion in selecting the entrance site of the osteal tunnel, limitations in visibility and accuracy considerations dictate that surgical positioning instruments are needed to ensure that an osteal tunnel has a precise drill exit point. Often, surgeons are required to work in an area that is "boxed in" by nerves, which gives rise to a need for surgeons to forego the use of conventional surgical positioning instruments that might interfere with these delicate areas.

There are several limitations to current techniques of fixing soft tissue to bone. The primary methods can be divided into two categories, the implementation of bone tunnels or the use of fixation devices such as suture anchors. The latter carries the risk of implant complications including infection and bony osteolysis in addition to failure of fixation. Transosseous tunnels are a more attractive option. Current transosseous tunnel techniques can be divided into two types. The first involves the creation of a straight tunnel using guides placed on the surface of the bone and drilling from one point to another. The second involves the creation of curved tunnels using drilling or awling devices that begin at both entry points of the tunnel and meet in the middle. However, these techniques are limited by technical constraints including the size of the bony bridge, the desired size of the tunnel, surgical exposure required to allow for access to the bone, and anatomical constraints such as nerve and vessel proximity. As such, these limitations further limit the use of transosseous techniques in the setting of arthroscopic surgery, especially in the shoulder. This is because this type of surgery is performed through limited exposure and is technically constrained by anatomic landmarks.

Surgical drill guides for use in drilling precision transosteal tunnels through bone are known in the art. For example, U.S. Pat. Nos. 5,163,940, 5,330,468 and 6,120,511 all disclose surgical drill guide devices. Drill guide devices, such as those taught in the above-referenced patents, generally comprise a housing having an axial opening, a probe connected to the housing and having a tip that is adapted to be disposed within the interior of the joint at the distal point where one end of the tunnel is to exit the target bone, and a guide wire sleeve for directing a guide wire into position on the surface of one of the bones of the joint. The housing is connected to the probe by an adjustable rack that is generally of a circular arc configuration. The housing is arranged so that its axial opening is more or less aligned to intersect with the aforementioned probe tip, and the guide wire sleeve is generally slidable or variable in position within the housing's axial opening. The relative angular position of the probe and the guide wire sleeve contained within the housing is slidably adjustable on the rack in order to accommodate differently sized human bones and joints. All of the aforementioned parts are held in relation to one another by releasable locking means known in the art.

The guide wire sleeve is positioned such that a guide wire can be inserted through the sleeve and positioned on the bone in order to properly position a drill. Once the guide wire sleeve is in position, the guide wire is slid through the guide wire sleeve and advanced (e.g., by drilling or tapping) through the bone. When the guide wire is in position in the bone, the sleeve is removed from the guide wire, leaving the guide wire in proper place within the bone. A cannulated drill bit is then positioned about the guide wire and a straight hole is drilled to the exit point initially marked by the tip of the probe. A suture is then affixed to, through, or around the torn ligament, and the suture, the ligament, or both are drawn into the osteal tunnel by a needle eye or alligator clamp that is run through either the sleeve, the osteal tunnel, or both. The suture is then tied in a knot, stapled to the bone, or the instrument used to pull the suture through the osteal tunnel remains in the tunnel as an anchor which must later be removed from the bone.

In use, the drill guide device tip is placed at the desired exit point of the tunnel and the guide wire sleeve is positioned at the desired entry point of the tunnel. A drill bit is inserted through the guide wire sleeve and a tunnel is drilled through the bone from the guide wire sleeve (entry point) to the tip (exit point). Generally, the tunnel is a straight bore in the form of a hypotenuse across the corner of the bone. With smaller bones, this tunnel can be very close to the surface of the bone, and therefore the tunnel wall closest to the surface of the bone can be thin and weak.

Each of the disclosed prior art guides are for performing straight transosteal tunneling, which can result in a weakening of the bone, especially when the tunnel created is close to the bone surface, or the guides require entry or exit points for the tunnel that are difficult to access. Further, prior art guides do not allow for flexibility in the positioning on the entrance point of the osteal tunnel, which is desirable when a surgeon meets with and/or wishes to avoid biological obstacles such as nerves or blood vessels. Also, many different and complex instruments are required to perform the completed surgery, which makes the surgery more difficult and susceptible to error. Finally, prior art methods of attaching the suture to or within the bone often require either a complex procedure to secure the suture, or a second surgery to remove an embedded anchoring device.

Accordingly, there is a need for an improved osteal guide, more particularly an osteal guide with improved stability and performance, resulting in improved tunnel strength. There is also a need for an improved method for drilling osteal tunnels, more particularly angled osteal tunnels, which allows a surgeon to be both flexible and accurate in the placement of the osteal tunnels, and which allows a surgeon to more easily increase the diameter of an osteal tunnel without compromising the surrounding anatomical structures. Additionally, there is a need for improved osteal guide components that simplify surgery while maintaining accuracy. Further, there is a need for an improved device for securing or anchoring sutures used in ligament reconstruction and for anchoring the ligaments themselves to or within the bone structure. Finally, there is a need for an improved method for securing tendons and other tissues to or within the bone structure. It is to these and other needs that the present invention is directed.

BRIEF SUMMARY OF THE INVENTION

Briefly, the present invention comprises methods for reaming an osteal tunnel so as to enlarge a section of the osteal tunnel after it is initially drilled to accommodate the anchoring of a desired portion of a damaged muscle, tendon or ligament within the osteal tunnel. By varying the diameter and depth of the osteal tunnel by using different sized reamers, the methods can be used on various sized bones and for anchoring various sized tissue. The present invention can be utilized in connection with:

(a) Methods for using osteal guides capable of facilitating the accurate drilling of an angled osteal tunnel, namely osteal tunnels having an angle or turn within the bone, which guides also can allow for the preparation or creation of an angled osteal tunnel having an intraosseous angle;

(b) Methods for drilling an angled osteal tunnel in which a first tunnel portion can be drilled free-hand into the bone, a second tunnel portion can be drilled into the bone using a guide wire having a burr as the drill bit and using a guide component to guide the drill bit to the interior end of the first tunnel portion (the end of the tunnel within the bone, the exterior being at the surface of the bone), such that the two portions of the tunnel intersect and connect at an angle, and in which either tunnel portion can be subsequently widened with a reamer, and either a suture or a suture and repaired tissue can be drawn into the tunnel, which methods also can include the intraosseous (that is, blind or without direct visualization) retrieval of sutures from within the osteal tunnel;

(c) Methods for using guide components that can be inserted into the first tunnel portion and can function as a guide into which the drill bit is aimed for drilling the second tunnel portion and for receiving and seizing a suture or another feeding device, such as a wire, inserted through the second tunnel portion (or alternatively if the suture is inserted through the first tunnel portion, the guide component can be inserted into the second tunnel portion for receiving and seizing a suture inserted through the first tunnel portion);

(d) Methods for using retrieving systems to grab or seize a suture or another suture-feeding device, which retrieving systems also can allow for the intraosseous (that is, blind or without direct visualization) retrieval of sutures from within a bone; and (e) Suture anchoring methods and the use of suture anchoring components that can secure or anchor a suture from within or outside of an osteal tunnel when a suture is positioned within an anchor and the anchor is compressed and deformed tightly about the suture.

For the purposes of this specification, the term "drilling" includes all forms of tunnel creation performed by physicians, such as, but not limited to, drilling with burrs, bits or wires, tamping, punching, and using awls.

As shown in FIG. 1, a typical prior art surgical drill guide comprises three primary components: a guide sleeve through which a drill bit is passed for drilling the osteal tunnels through a bone, a guide tip for guiding the drilling direction of the drill bit, and a rack onto which the guide sleeve and the guide tip are mounted. The guide sleeve and/or guide tip are typically slidably mounted on the rack, which may be arcuate, such that different angles of osteal tunnels can be drilled through the bone. The guide sleeve also can be displaceably mounted on the rack such that different sized bones can be accommodated and different lengths of osteal tunnels can be drilled.

In a device suitable for use with the present invention, the typical guide tip is replaced with a novel guide component that facilitates the drilling of an angled osteal tunnel, namely an osteal tunnel having a first portion drilled from one surface of the bone, a second portion drilled from a second surface of the bone, wherein the first portion and the second portion intersect and connect at an angle in the interior of the bone. This guide component is structured to be insertable into the first tunnel portion so as to guide the drilling of the second tunnel portion at the appropriate angle and depth to connect and intersect with the first tunnel portion within the interior of the bone. The resulting tunnel generally will have straight or approximately straight first and second portions intersecting at an angle such that the tunnel as a whole will be more within the interior of the bone and farther away from the surface of the bone than a typical transosteal tunnel, resulting in a stronger tunnel. An angled osteal tunnel created in this manner gives a surgeon the ability to allow small distances between the entry sites into the bone and at the same time have a sufficiently strong bony bridge to maintain the integrity of the surgical site.

In an illustrative method of the present invention, the first tunnel portion can be and preferably is drilled or punched free-hand at a predetermined distance into any bone in a human body located a suitable distance from a torn tendon or ligament, such as those in the hand, elbow, arm, shoulder, ankle, and knee. Various devices can be used in conjunction with the free-hand drilling or punching such that the first tunnel is drilled in a proper direction, at a proper angle and for a proper distance. For example, drill stops known in the art can be attached to the drill bit or the drill guide to set or limit the depth of the drilling.

After the first tunnel portion is drilled or punched into the bone, the guide component is inserted into the first tunnel portion a certain distance, usually a distance equal or approximately equal to (but not necessarily) the length of the first tunnel portion. The guide sleeve then is adjusted on the rack to allow for a drilling angle and distance desired for the second tunnel portion. The second tunnel portion then is drilled or punched using the guide sleeve, guide component, and rack configuration (that is, not free-hand) whereby the second tunnel portion is drilled at a specific angle and length so as to intersect and connect with the first tunnel portion. The drill can be any conventional drill known in the art, including a burr fixed or attached to the end of a guide wire, which is an illustrative example of a drill suitable for use with the methods disclosed herein. The configuration of the guide sleeve and guide component on the rack provides that the guide sleeve is angled directly at the interior (inserted) end of the guide component such that the second tunnel is drilled directly at the interior end of the guide component. The guide component can include a target at the interior end, specifically, a hole or open area, such that the drill bit passes through the target and does not contact the guide component. The devices and methods of this invention thus can allow the surgeon to drill an angled osteal tunnel without direct visualization of the intersection of the first tunnel portion and the second tunnel portion.

After the second tunnel portion is drilled, the guide component can be left in place in the first tunnel portion such that a suture or wire inserted into the length of the second tunnel portion can reach the guide component. The guide component also can have a suture seizing mechanism, so that the suture or wire can be seized by this suture seizing mechanism, and the suture or wire can be pulled through the first tunnel portion. Thus, the guide component can allow for the retrieval of a suture from within a bone without direct visualization of the interior of the osteal tunnel or the osteal tunnel end points. Alternatively, a wire having a loop at one end can be pulled through the osteal tunnels so that a suture can be inserted into the loop and pulled back through the osteal tunnels. One end of the suture or wire can be attached to the ligament or muscle in known manners, and another end of the suture can be attached to the bone in known manners, or tied together to the ends of other sutures emanating from other tunnels, or anchored together with sutures emanating from other tunnels using the novel anchor and anchoring method disclosed herein. A suture also can be tied off in a "mattress" tying method, by looping a suture around a torn ligament or tendon in a mattress suture pattern, and then pulling the suture, and often with it, a portion of the tendon, into the tunnel. In another illustrative embodiment, one or more ends of a suture that have been drawn through an angled osteal tunnel can be wrapped around both the torn ligament or tendon and the bony bridge between the tunnel entrances and tied or stapled off.

In an embodiment illustrative of the methods disclosed herein, the second tunnel portion is drilled with a burr attached to a guide wire. The guide wire preferably is a relatively rigid wire or thin rod to better guide the reamer, as disclosed herein. The guide component is removed and the guide wire is left in place in the osteal tunnel. A reamer having a guide tunnel therethrough is placed over the guide wire and the tip of the reamer is placed in or at the entrance of the osteal tunnel and guided into the osteal tunnel by the guide wire as the reamer is turned, either manually or mechanically. As the reamer is turned, the corresponding section of the osteal tunnel is widened to the diameter of the reamer. The osteal tunnel can be widened to any depth, as determined by the surgeon, while the guide wire helps ensure that the reamer remains centered in the osteal tunnel.

In a guide component suitable for use in the present invention, the interior end (the end that is inserted into the osteal tunnel) can comprise a target and a suture seizing ring. For example, the guide component can be a cylinder having a grip and trigger mechanism on the exterior end and a target ring and piston or pestle on the interior end. Alternatively, hinged scissor handles can be used on the exterior end. The target ring can be structured to accommodate the drill bit exiting the second tunnel portion as the drill bit causes the second tunnel portion to intersect and connect with the first tunnel portion. The trigger mechanism or scissor handles can be squeezed or engaged to force the piston or pestle axially in the cylinder and into the target ring so as to pin a suture or wire against the inner surface of the target ring, thus seizing the suture. Thus, the suture can be inserted into the second tunnel portion, or can be gripped by a suture inserter and inserted into the second tunnel portion, a distance where the suture interacts with the guide component such that the suture can be seized by the guide component. As the guide component is removed from the first tunnel portion, the captured suture and, if desired, a portion of the tendon, muscle, ligament to which the suture is attached is pulled through or into the tunnel. Suture inserters are known and can have a mechanism for gripping and releasing the suture, such as a claw grip.

An illustrative alternative of a suitable method for creating osteal tunnels includes drilling or punching multiple second tunnel portions all intersecting and connecting with a single first tunnel portion. For example, a single first tunnel portion can be drilled as disclosed previously. After the first tunnel portion is drilled, the guide component is inserted into the first tunnel portion a certain distance as disclosed previously. The guide sleeve is then moved to a first location on the surface of the bone and is adjusted on the rack to allow for a drilling angle and distance desired for a first second tunnel portion. This first second tunnel portion then is drilled using the guide sleeve, guide component, and rack configuration as disclosed previously so as to intersect and connect with the first tunnel portion. The guide sleeve then is moved to a second location on the surface of the bone and is adjusted on the rack to allow for a drilling angle and distance desired for a second second tunnel portion. This second second tunnel portion then is drilled using the guide sleeve, guide component, and rack configuration in the same manner as the first second tunnel portion so as to intersect and connect with the first tunnel portion. The guide sleeve then can be moved to drill third and additional second tunnel portions, all of which intersect with the first tunnel portion. A guide wire can be inserted in any desired tunnel portion so that the desired tunnel portion can be widened with a reamer.

A suture (or multiple sutures) or wire is inserted into each of the second tunnel portions so as to reach the guide component. The suture is seized by the suture seizing mechanism of the guide component and is pulled through the first tunnel portion. If multiple sutures are used, it is preferable that all of the sutures are seized at once. One end of each of the sutures can be attached to the ligament or muscle in known manners, and other ends of the sutures can be attached to the bone in known manners, or tied together to ends of other sutures emanating from other tunnels, or anchored together with sutures emanating from other tunnels using the novel anchor and anchoring method disclosed herein. Sutures also can be tied off in the "mattress" tying method, or by wrapping the suture around both the torn ligament or tendon and the bony bridge between the tunnel entrance and tied or stapled off, as disclosed earlier. Portions of the ligament can be pulled into the reamed tunnel(s) and the bone allowed to heal and reform over the ligament. The second tunnel portions can be in a fan-shaped configuration or in a linear configuration, or any geometric configuration, relative to the first tunnel portion.

Another illustrative alternative of a suitable method for drilling osteal tunnels includes drilling a number of second tunnel portions for intersecting with a smaller number of first tunnel portions such that at least one first tunnel portion intersects and connects with at least two second tunnel portions. This alternative is similar to the alternative disclosed above, but at least two first tunnel portions are drilled, and at least three second tunnel portions are drilled, with at least two of the second tunnel portions intersecting and connecting with one of the first tunnel portions. One or more of these tunnel portions also can be reamed according to the present invention.

In an anchor component suitable for use with the present invention, at least one suture extending through the tunnel can be secured using an anchor, thus avoiding the use of knots or a staple into the bone. An illustrative anchor is an oval device through which one or more sutures can extend. The anchor is then compressed or deformed to anchor the suture, by for example friction and/or compression, thus preventing the suture from being pulled back through the tunnel. In the multi-tunnel embodiments, the multiple sutures all can be passed through a single anchor. Alternatively, knots can be used to secure a suture in accordance with the present invention. Alternatively, a portion of the ligament also can be pulled through the reamed tunnel(s) and anchored using the illustrative anchor. In such an embodiment it may be necessary to ream both the first and the second tunnel portions.

The present invention can be performed during open surgery and during arthroscopic surgery. The present invention also can be performed generally anywhere on a human body affected by a torn muscle, ligament or tendon.

The present invention involves both methodology and the use of tools necessary to allow for the creation of reamed (widened) angled tunnels, including the blind creation of reamed angled osteal tunnels and the intraosseous retrieval of sutures from osteal tunnels. This entails the use of an intraosseous guide, a feeder and retrieval system, and a reamer. The resultant tunnels provide robust bony bridges even with minimal distance between the surface points of entry and exit on the bone and reamed tunnels having a diameter sufficient for a suture or sutures or for portions of ligaments or other tissue to extend therethrough. The resultant tunnels can be created through limited exposure, and the technique may be performed arthroscopically, especially in the shoulder and upper arm areas. Arthroscopic surgery of the shoulder to repair a torn rotator cuff or a ruptured bicep, such as or including bicep tenodesis, involves fixation of the torn tendon to bone. Straight tunnels are precluded because the closer the point of entry and exit, the more shallow the tunnel and the weaker the bony bridge. The setting of arthroscopic rotator cuff repair and biceps tenodesis allow for excellent illustrative examples of the utility of the present invention.

Thus, the present invention involves the creation of enlarged angled tunnel portions with a manual or automatic reamer. The resultant enlarged tunnel portions can accommodate both a suture or wire and a portion of a tendon, muscle or ligament in need of repair. The ability of the widened tunnel portion to accommodate both the suture and the portion of a tendon, muscle or ligament allows both the bone and the tendon or muscle or ligament to grow together during the healing process, which results in an extremely strong and durable fusion. This technique also allows for the avoidance of critical nerves or vessels on the surface of a bone, because only two relatively small drilled holes in the surface of the bone are needed to create the widened tunnel portion within the bone, rather than, for example, having to attach the tissue to a larger surface area of the outer surface of the bone, where it can interfere with the nerves running proximal to the bone.

These features, and other features and advantages of the present invention will become more apparent to those of ordinary skill in the art when the following detailed description of the preferred embodiments is read in conjunction with the appended figures.

BRIEF DESCRIPTION OF THE DRAWINGS

FIG. 2B is a top plan view of the surgical drill guide device shown in FIG. 2A, further showing the attachment of the drill guide.

FIG. 2C is bottom plan view of an embodiment of a guide component with suture seizing mechanism that can be used in conjunction with the present invention.

FIG. 3 is a perspective view of a human bone showing an angled osteal tunnel drilled using a method of present invention and having a single entrance and exit point and prior to reaming.

FIG. 5 is a schematic cross-sectional view of a human bone showing an embodiment of a suture seizing mechanism and method that can be used in conjunction with the present invention in use prior to the seizing of a suture.

FIG. 6 is a schematic cross-sectional view of a human bone showing an embodiment of a suture seizing mechanism and method that can be used in conjunction with the present invention in use subsequent to the seizing of a suture.

FIG. 7 is a schematic cross-sectional view of a human bone showing osteal tunnels having one entrance point and multiple exit points formed by an alternate embodiment of a method of the present invention and prior to reaming.

FIG. 16 is an alternate embodiment of the surgical drill guide device shown in FIG. 2A having a movable guide component and showing a straight rod and plunger suture seizing mechanism.

FIG. 17 is an alternate embodiment of the surgical drill guide device shown in FIG. 2A having a movable drill guide and a movable guide component.

FIG. 18A is a perspective view of a clamp and tightening screw that can be used with the movable drill guide and/or movable guide component.

FIG. 18B is a cross-sectional side view of a clamp and tightening screw shown in FIG. 18A.

DETAILED DESCRIPTION OF PREFERRED EMBODIMENTS

The following detailed description of preferred embodiments is presented only for illustrative and descriptive purposes and is not intended to be exhaustive or to limit the scope and spirit of the invention. The embodiments were selected and described to best explain the principles of the invention and its practical applications. One of ordinary skill in the art will recognize that many variations can be made to the invention disclosed in this specification without departing from the scope and spirit of the invention.

Figure 2A:
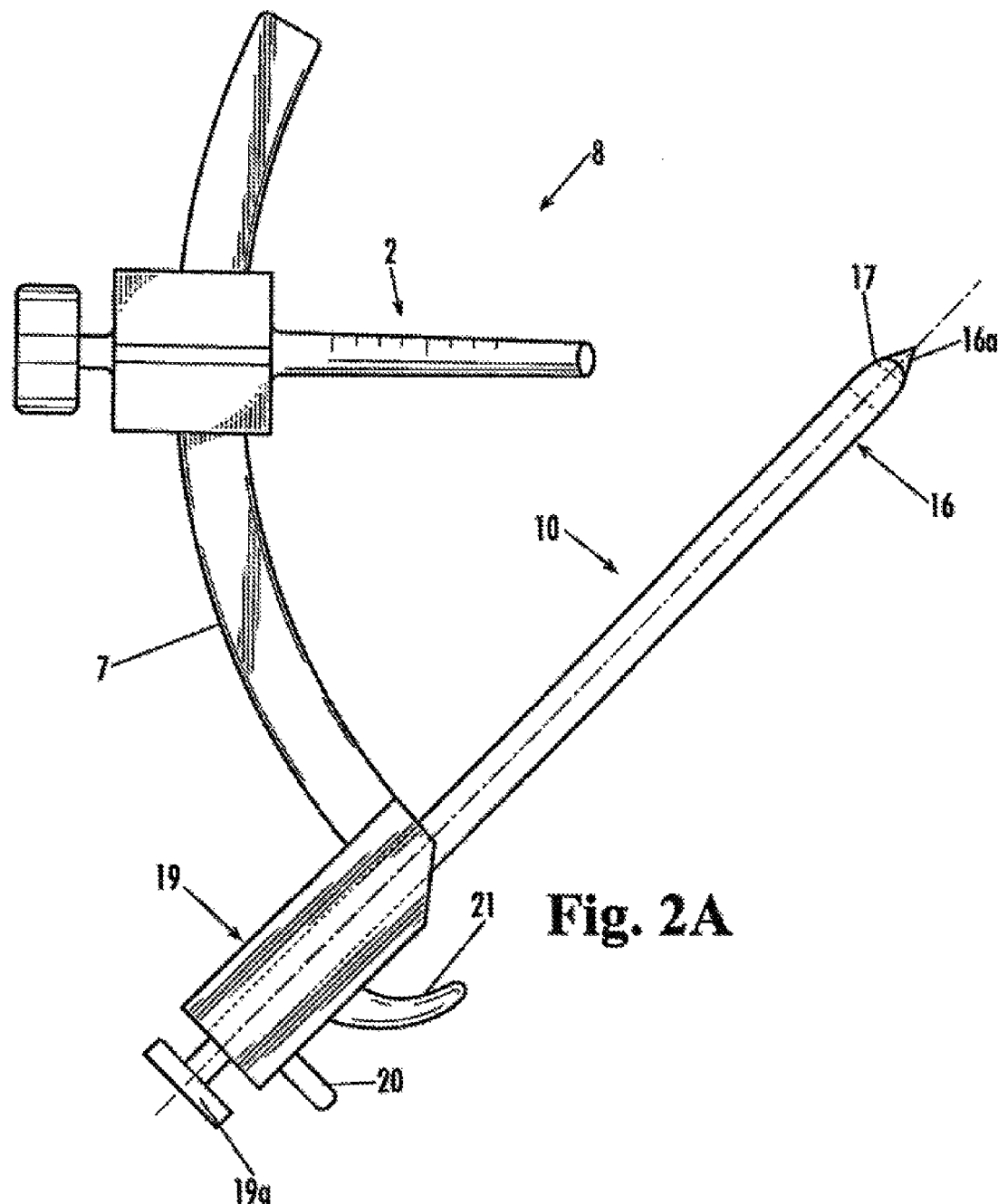
FIG. 2A is an elevational view of a surgical drill guide device that can be used in conjunction with the present invention having a movable drill guide.

Illustrative embodiments of a device and method for drilling angled osteal tunnels, including widened (reamed) tunnel portions, and anchoring sutures and/or tendons (and/or other tissues) therein that can be used and performed in connection with the present invention are shown in FIGS. 2A through 24. FIG. 2A is an elevation view of a surgical drill guide device having a movable drill guide. FIG. 2B is a top plan view of the surgical drill guide device shown in FIG. 2A, further showing the attachment of the drill guide. FIG. 2C is bottom plan view of the guide component with suture seizing mechanism that can be used in conjunction with the present invention.

Figure 4:
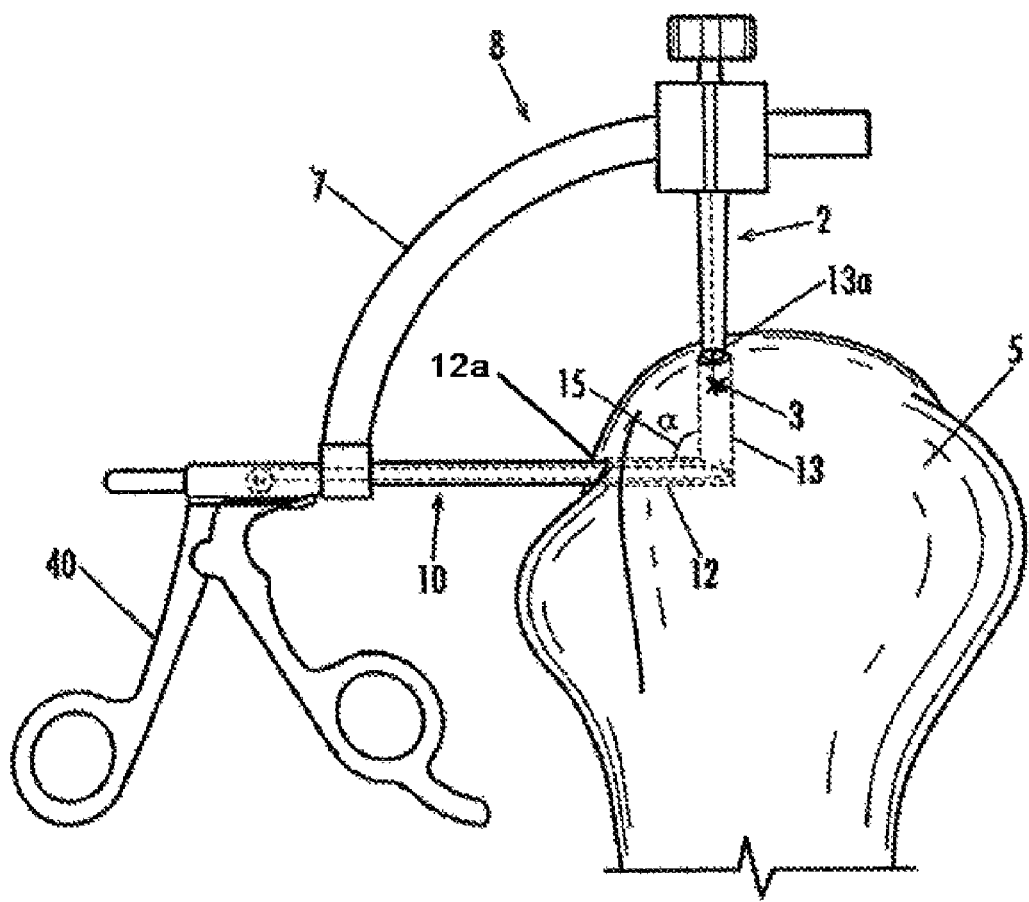
FIG. 4 is a perspective view of a human bone with an angled osteal tunnel similar to that shown in FIG. 3, showing the typical positional relationships of both the drill guide and guide component with suture seizing mechanism of FIG. 2A and showing scissor handles on an illustrative suture seizing mechanism.
Figure 4A:
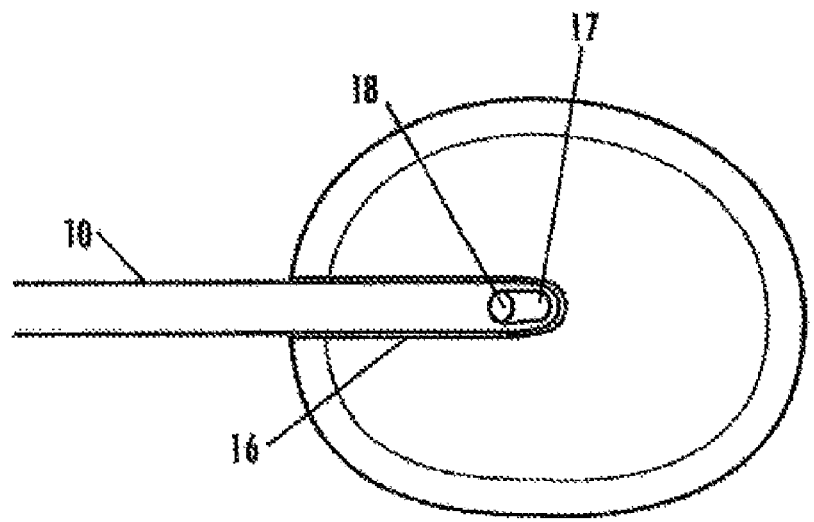
FIG. 4A is a top cross-sectional view of a human bone as shown in FIG. 4 showing a typical positional relationship of the guide component with a suture seizing mechanism within the angled osteal tunnel.

FIG. 3 is a perspective view of a human bone showing an angled osteal tunnel drilled using a method of present invention and having a single entrance and exit point, prior to reaming. FIG. 4 is a perspective view of a human bone with an angled osteal tunnel similar to that shown in FIG. 3, showing typical positional relationships of both the drill guide and guide component with suture seizing mechanism of FIG. 2A and showing scissor handles on the suture seizing mechanism, prior to reaming. FIG. 4A is a top cross-sectional view of a human bone as shown in FIG. 4 showing typical positional relationships of the guide component with suture seizing mechanism within the angled osteal tunnel.

Figure 8:
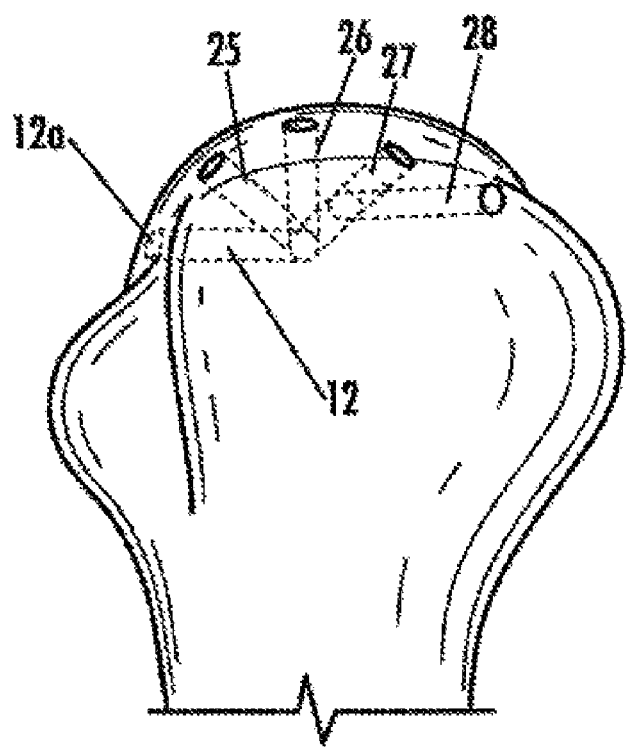
FIG. 8 is a perspective view of a human bone showing osteal tunnels having multiple entrance points and one exit point formed by an alternate embodiment of a method of the present invention and prior to reaming.
Figure 9:
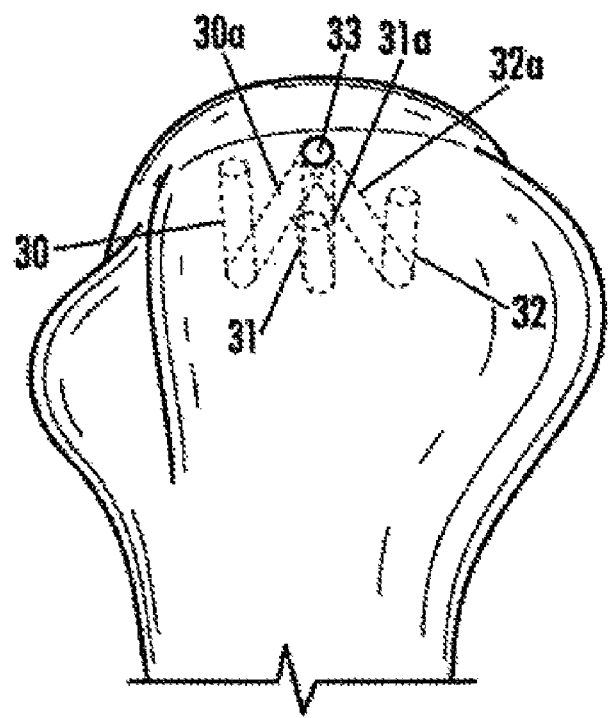
FIG. 9 is a perspective view of a human bone showing osteal tunnels having one entrance point and multiple exit points formed by an embodiment of the method of a present invention and prior to reaming.

FIG. 5 is a schematic cross-sectional view of a human bone showing an embodiment of the suture seizing mechanism and method that can be used in conjunction with the present invention in use prior to the seizing of a suture. FIG. 6 is a schematic cross-sectional view of a human bone showing an embodiment of the suture seizing mechanism and method that can be used in conjunction with the present invention in use subsequent to the seizing of a suture. FIG. 7 is a schematic cross-sectional view of a human bone showing osteal tunnels having one entrance point and multiple exit points formed by an alternate embodiment of the method of the present invention, prior to reaming. FIG. 8 is a perspective view of a human bone showing osteal tunnels having multiple entrance points and one exit point formed by an alternate embodiment of a method of the present invention, prior to reaming. FIG. 9 is a perspective view of a human bone showing osteal tunnels having one entrance point and multiple exit points formed by an embodiment of a method of the present invention, prior to reaming.

Figures 10, 11, 12:
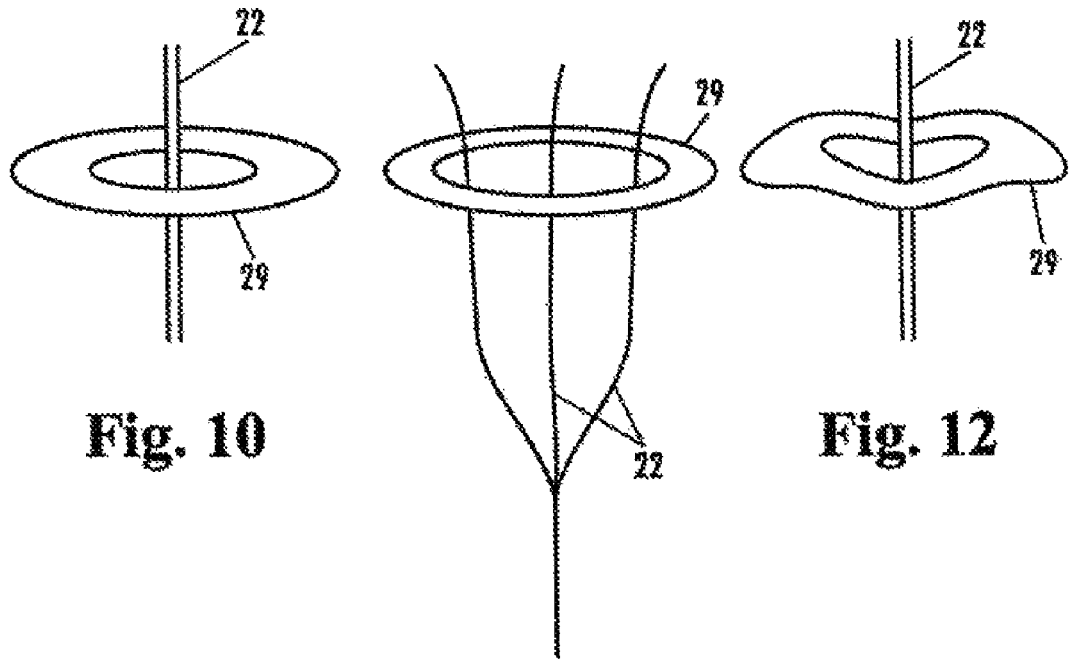
FIG. 10 is a perspective view of an embodiment of an anchor that can be used in conjunction with the present invention showing the typical positioning of a suture to be anchored.
FIG. 11 is a perspective view of an embodiment of an anchor that can be used in conjunction with the present invention showing an alternate method for anchoring multiple sutures within the same anchor.
FIG. 12 is a perspective view of the anchor of FIG. 10 in a deformed and anchored position about a suture.
Figures 13, 14:
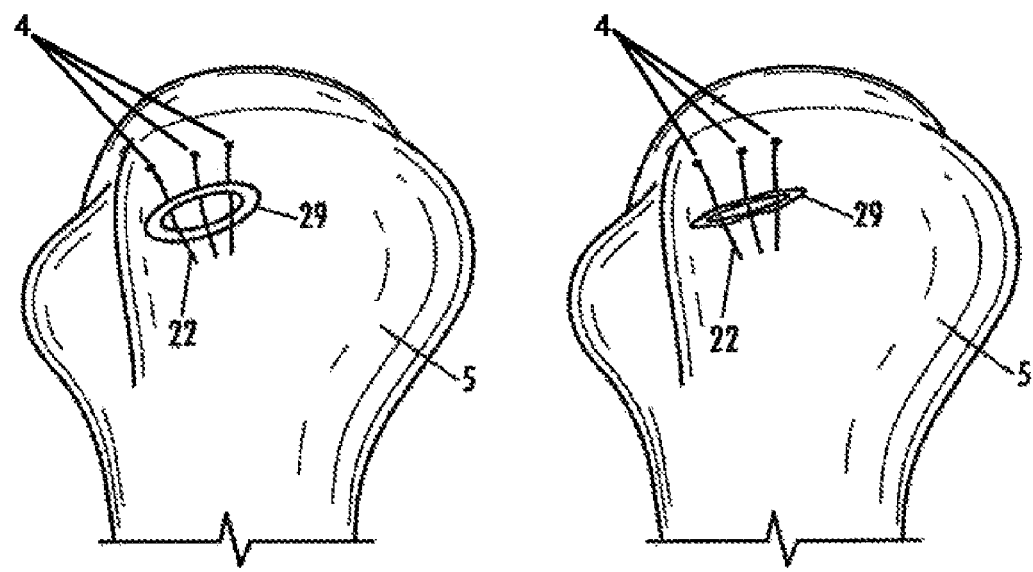
FIG. 13 is a perspective view of a human bone showing the anchor and alternate method for anchoring multiple sutures within the same anchor of FIG. 11 in use, with multiple sutures emerging from multiple osteal tunnel exit points.
FIG. 14 is a perspective view of a human bone, anchor, and sutures of FIG. 13, showing the anchor in a deformed and anchored position about the multiple sutures.

FIG. 10 is a perspective view of an embodiment of an anchor that can be used in conjunction with the present invention showing the typical positioning of a suture to be anchored. FIG. 11 is a perspective view of an embodiment of this anchor showing an alternate method for anchoring multiple sutures within the same anchor. FIG. 12 is a perspective view of the anchor of FIG. 10 in a deformed and anchored position about a suture. FIG. 13 is a perspective view of a human bone showing the anchor and alternate method for anchoring multiple sutures within the same anchor of FIG. 11 in use, with multiple sutures emerging from multiple osteal tunnel exit points. FIG. 14 is a perspective view of a human bone, anchor, and sutures of FIG. 13, showing the anchor in a deformed and anchored position about the multiple sutures.

Figure 15A:
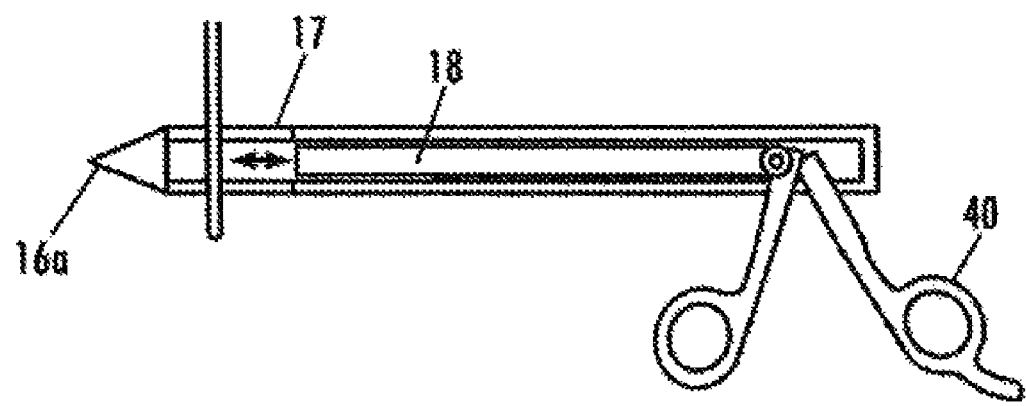
FIG. 15A is a cross-sectional side view of an embodiment of a guide component showing an illustrative suture seizing mechanism.
Figure 15B:
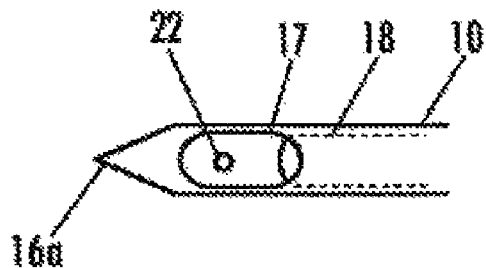
FIG. 15B is a top plan view of an illustrative insertion end of an embodiment of a guide component with the seizing pestle in the retracted position.
Figure 15C:
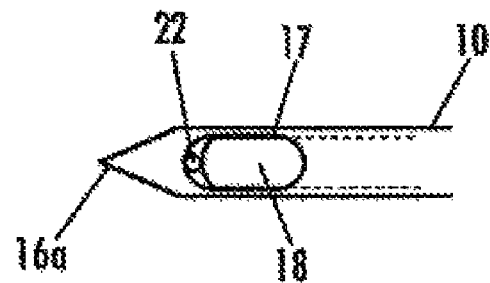
FIG. 15C is a top plan view of an illustrative insertion end of an embodiment of a guide component with the seizing pestle in the extended or seizing position.

FIG. 15A is a cross-sectional side view of an embodiment of a guide component showing an illustrative suture seizing mechanism. FIG. 15B is a top plan view of an illustrative insertion end of an embodiment of a guide component with the seizing pestle in the retracted position. FIG. 15C is a top plan view of an illustrative insertion end of an embodiment of a guide component with the seizing pestle in the extended or seizing position.

FIG. 16 is an alternate embodiment of the surgical drill guide device shown in FIG. 2A having a movable guide component and showing a straight rod and plunger suture seizing mechanism. FIG. 17 is an alternate embodiment of the surgical drill guide device shown in FIG. 2A having a movable drill guide and a movable guide component.

FIG. 18A is a perspective view of a clamp and tightening screw that can be used with the movable drill guide and/or movable guide component. FIG. 18B is a cross-sectional side view of a clamp and tightening screw shown in FIG. 18A.

Figure 19:
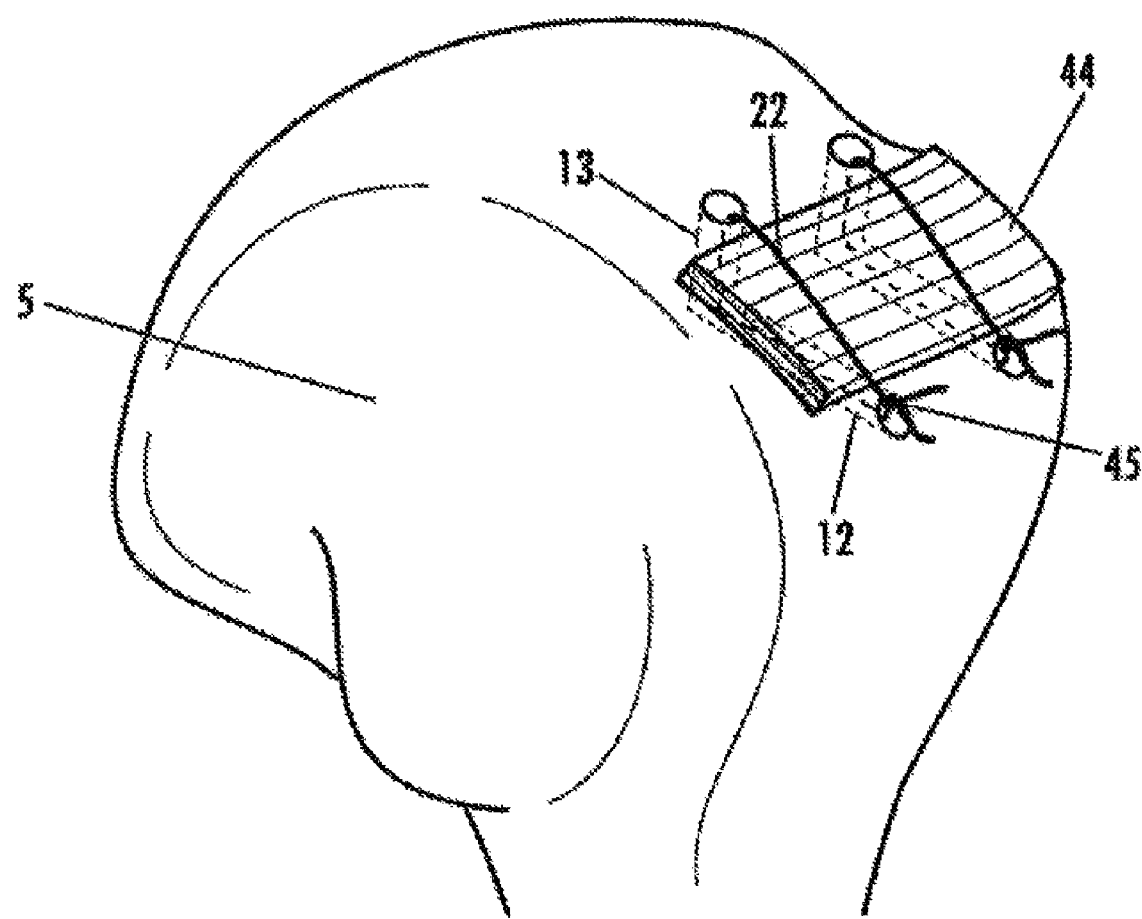
FIG. 19 is a perspective view of a human bone showing an alternate method for tying and anchoring a ligament with a suture between osteal tunnels.

FIG. 19 is a perspective view of a human bone showing an alternate method for tying and anchoring a ligament with a suture between osteal tunnels.

Figure 20:
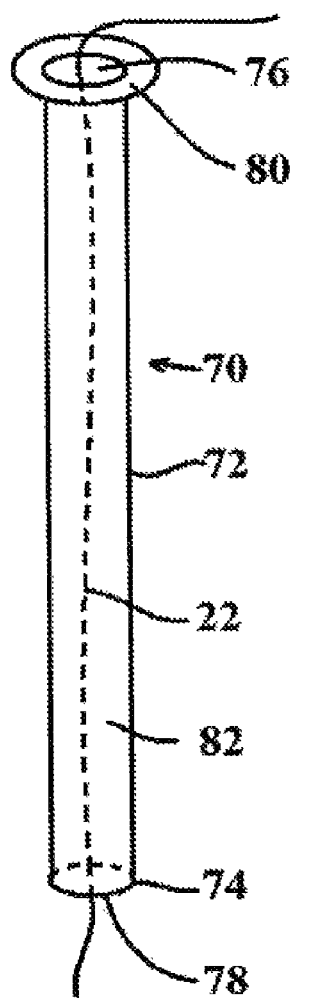
FIG. 20 is a perspective view of a suture feeding sleeve that can be used in conjunction with the present invention.
Figure 21:
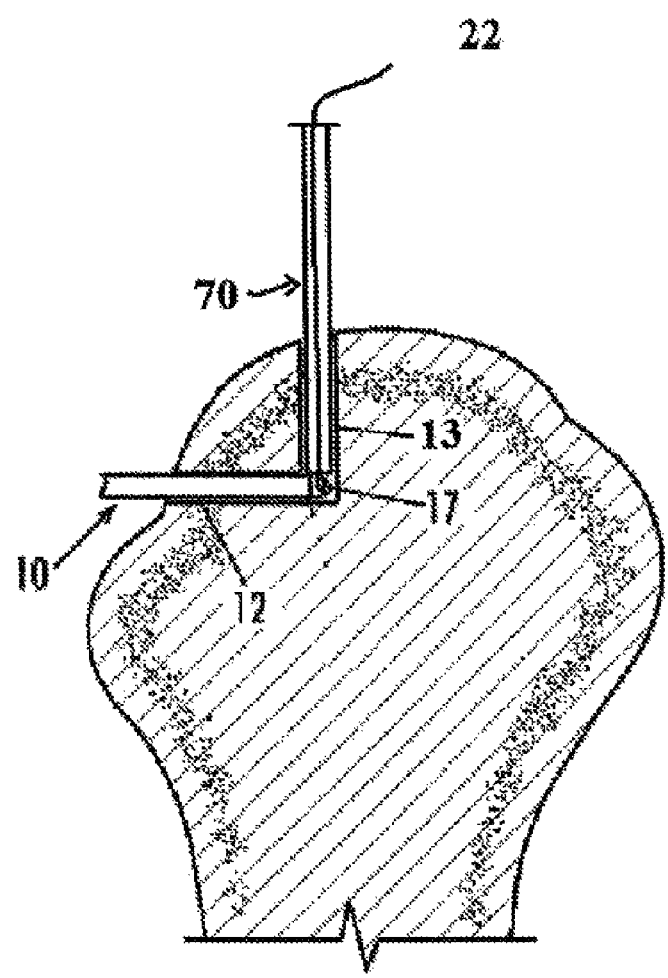
FIG. 21 is a cross-sectional side view of the suture feeding sleeve of FIG. 20 in use.

FIG. 20 is a perspective view of a suture feeding sleeve that can be used in conjunction with the present invention. FIG. 21 is a cross-sectional side view of the suture feeding sleeve of FIG. 20 in use.

Figure 22:
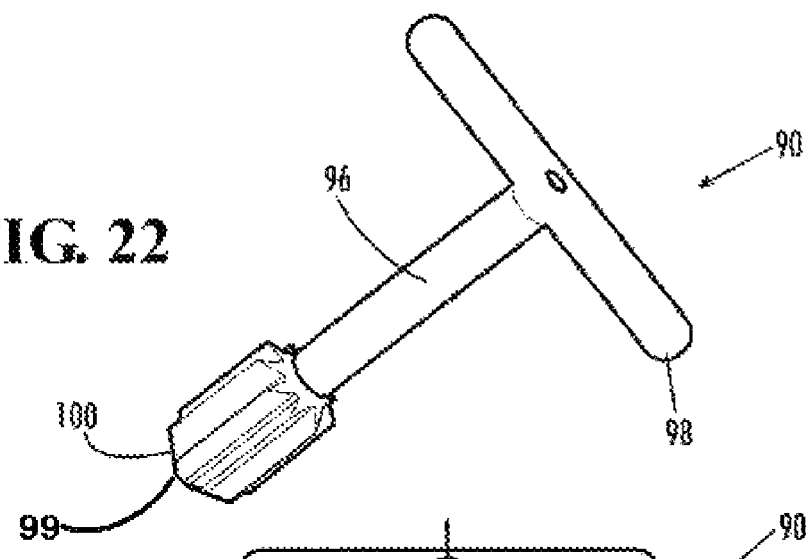
FIG. 22 is a perspective view of an embodiment of a manual bone reamer in accordance with the present invention.
Figure 23:
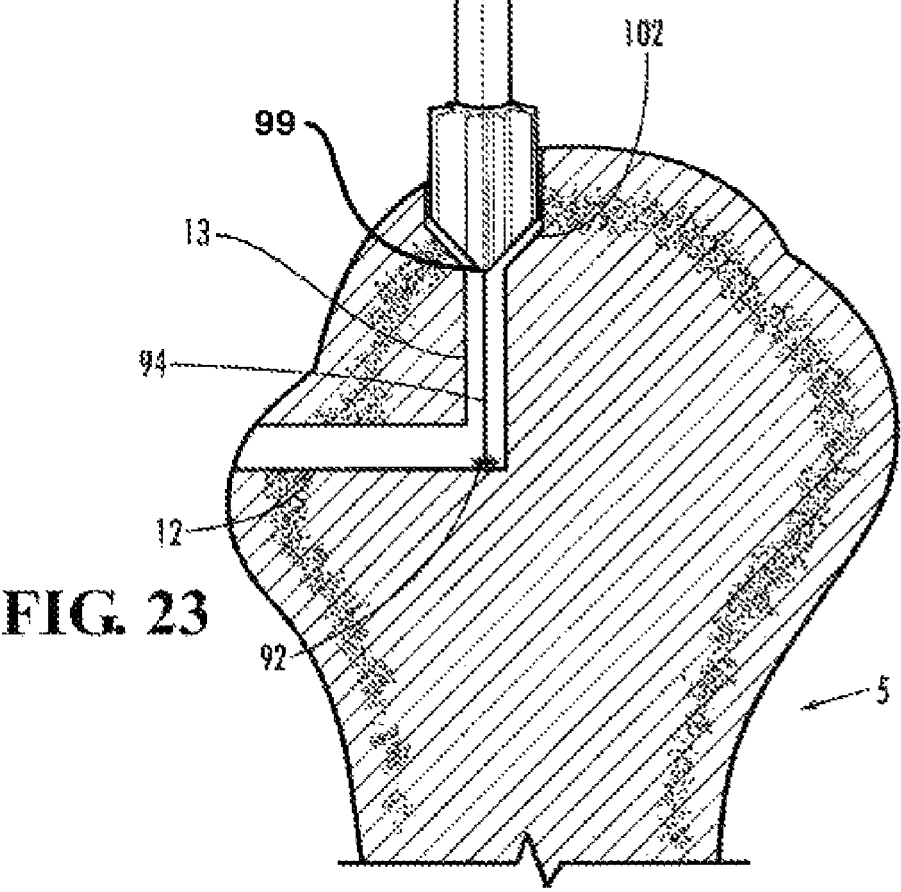
FIG. 23 is a schematic cross-sectional view of a human bone showing an embodiment of a manual bone reamer and method of the present invention in use subsequent to the initial formation of the angled osteal tunnels.
Figure 24:
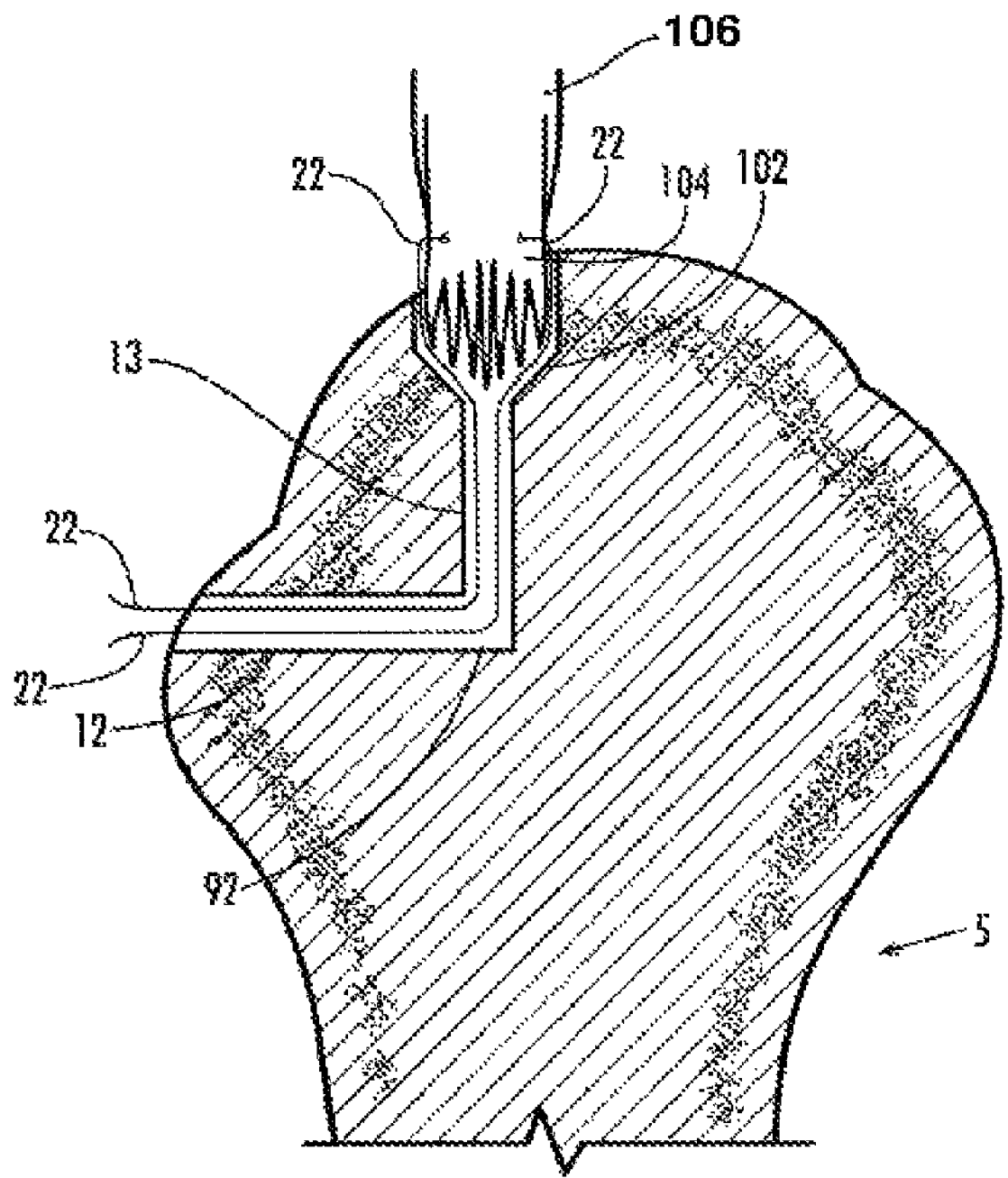
FIG. 24 is a schematic cross-sectional view of the human bone with the reamed osteal tunnel of FIG. 23 illustrating sutures attached to a tendon, the sutures being pulled through the angled osteal tunnel and the tendon being pulled into the reamed tunnel portion.

FIG. 22 is a perspective view of an embodiment of a manual bone reamer in accordance with the present invention. FIG. 23 is a schematic cross-sectional view of a human bone showing an embodiment of a manual bone reamer and method of the present invention in use subsequent to the initial formation of the angled osteal tunnels. FIG. 24 illustrates how the sutures and tendon can be pulled through and/or into the angled osteal tunnel and/or the reamed (widened) tunnel portion, as appropriate.

The subject matter of the present invention are methods for drilling and enlarging osteal tunnels and anchoring portions of tendons, muscles, ligaments, or other tissues therein. In preferred embodiments, the inventive methods comprise using novel drill guide devices and appurtenant components, and methods for using the same, as disclosed and claimed in related patent applications. For clarity, a detailed description of such novel drill guide devices and appurtenant components, and methods for using the same, will be disclosed herein.

The present invention is a method for using an improved drill guide device for drilling osteal tunnels, further enlarging the osteal tunnels using reaming devices, and anchoring sutures and/or tissues through or within the enlarged tunnels. The present invention is suitable for use in conjunction with ACL and rotator cuff ligament repair surgery in humans, biceps tenodesis, as well as other human ligament, muscle and tendon repairs. Currently, there is a need for methods for creating angled osteal tunnels in conjunction with human ligament, muscle and tendon repair that allows users to be both accurate and flexible, as well as methods to simplify surgery, improve surgical results, and minimize errors. There is a further need for intraosseous methods for creating osteal tunnels and retrieving sutures from within osteal tunnels without having to see or visualize within the bone or osteal tunnels. There is yet a further need for intraosseous methods for enlarging sections of osteal tunnels to accommodate both a muscle, ligament or tendon in need of repair and a suture or sutures for improved strength and stability upon healing of the bone.

Figure 1:
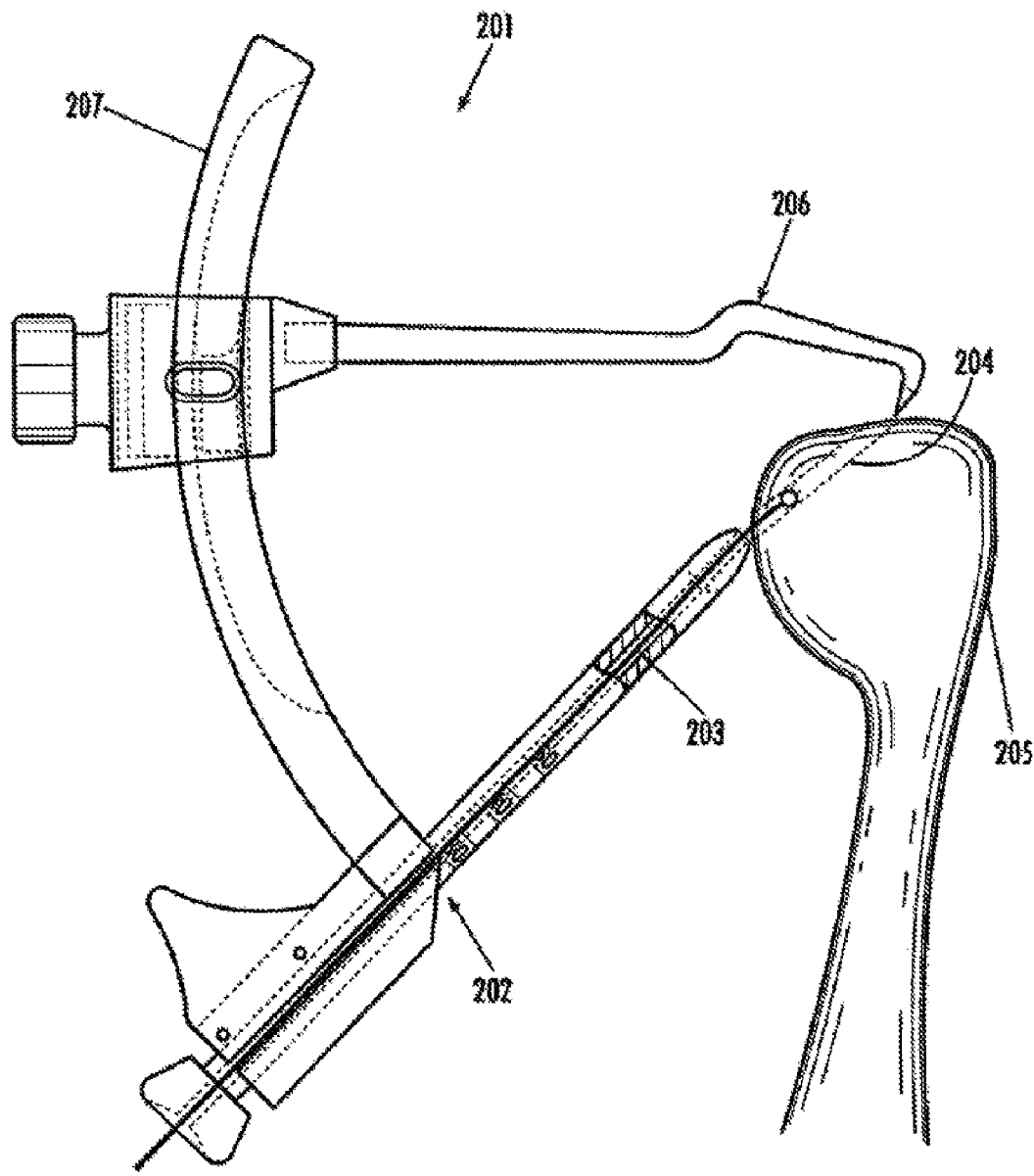
FIG. 1 is a prior art surgical drill guide device.

FIG. 1 shows an illustrative example of a known surgical drill guide 201 comprising three primary components: a drill guide sleeve 202 through which a guide wire and/or drill bit 203 is passed for drilling the osteal tunnel 204 through the bone 205; a guide tip 206 for guiding the drilling direction of the drill bit 203 or guide wire; and a rack 207 onto which the drill guide sleeve 202 and the guide tip 206 are mounted, which may be arcuate in shape. The drill guide sleeve 202 and/or guide tip 206 are typically slidably mounted on the rack 207 such that different angles of osteal tunnels 204 can be drilled through the bone 205. The drill guide sleeve 202 also can be displaceably mounted on the rack 207 such that different sized bones 205 can be accommodated and different lengths of osteal tunnels 204 can be drilled.

Referring now to FIGS. 2A, 2B, and 2C, an illustrative example of a surgical tool 8 suitable for use with the present invention comprises a guide component 10 mounted to an end of rack 7, which may be arcuate in shape, and a drill guide sleeve 2 slidably or removably mounted to the rack 7, which is capable of being securely positioned about the rack 7, toward either end. The guide component 10 facilitates the drilling of an angled osteal tunnel 11 (FIGS. 3 and 4), namely an osteal tunnel 11 having a first tunnel portion 12 drilled from a first surface 12a of the bone 5, a second tunnel portion 13 drilled from a second surface 13a of the bone 5, wherein the first tunnel portion 12 and the second tunnel portion 13 meet at an intersection 14 and connect at an angle 15 in the interior of the bone 5. The guide component 10 is structured to be insertable into the first tunnel portion 12 (FIG. 4) so as to guide the drilling of the second tunnel portion 13 at the appropriate angle 15 and depth to connect with the first tunnel portion 12 at the intersection 14 within the interior of the bone 5. The resulting osteal tunnel 11 generally will have straight or approximately straight first and second portions 12, 13 intersecting at an angle 15 such that the osteal tunnel 11 as a whole tends to be situated deeper within the interior of the bone 5 and farther away from the surface of the bone 5 than a typical transosteal tunnel, resulting in a stronger osteal tunnel 11.

The guide component 10 of one embodiment of the surgical tool 8 comprises an interior end 16, which is inserted into an osteal tunnel 11 within a bone 5 during a surgical procedure. The interior end 16 comprises a target ring 17 and a suture seizing pestle 18. The guide component 10 further comprises an exterior end 19, which is mounted on an end of rack 7. A grip 20 and a trigger mechanism 21 facilitate the operation of the target ring 17 and suture seizing pestle 18, such that a suture 22 (see FIG. 5) or wire can be seized within an osteal tunnel 11 and pulled from an entrance point at the surface of the bone 5 to an exit point at another location at the surface of the bone 5. For example, the guide component 10 can be a hollow cylinder attached to the rack 7 at the exterior end 19 and having a blunt or rounded tip. The guide component 10 also has an opening near the tip of the interior end 16 that forms the target ring 17. The opening within the target ring 17 may be round, oval, or otherwise shaped so as to accommodate a suture.

The guide component 10 of another embodiment of the surgical tool 8 comprises an interior end 16 having an awl tip 16a and an exterior end 19 having a tamping plate 19a. Depending on the conditions and quality of the bone 5 in which the osteal tunnel is formed, it may be preferable to tamp or punch any portion of the angled osteal tunnel 4 using a punching device with a sharp tip, such as an awl. A surgeon can punch an osteal tunnel 4 by either pushing the awl tip 16a into the bone 5, or using a hammer or other suitable object to tap the tamping plate 19a, thus driving the awl tip 16a of the guide component 10 into the bone 5. The guide component 10 can remain in a tamped or punched first tunnel portion 12, and the drill guide sleeve 2 can be coupled with a drill to create a second tunnel portion 13. Alternatively, a second tunnel portion 13 is tamped or punched in a similar manner using a punching device, such as an awl tip 16a with a tamping plate 19a.

In a preferred embodiment, the drill guide sleeve 2 is a hollow tube through which an osteo drill can be operated, and is of a structure generally known in the art. In an embodiment in which the drill guide sleeve 2 is movable on the rack 7, the drill guide sleeve 2 is slidably mounted on the rack 7 by a clamp 23 and tightening screw 24 so that the positioning of the drill guide sleeve 2 is adjustable about the length of the rack 7. Alternatively, the drill guide sleeve 2 can be fastened to the rack 7 by a clip, a bolt, or any other means known in the art to securely fix the drill guide sleeve 2 in the desired position on the rack 7. It is preferable that the drill guide sleeve 2 is movable on the rack 7 and that the guide component 10 is fixed on the rack 7 because, as the guide component 10 is placed into a first tunnel portion 12 that has been drilled free-hand without the use of a drill guide sleeve 2, the guide component 10 supports the rack 7 so that the drill guide sleeve 2 can be moved to any convenient position about the rack 7 for drilling the second tunnel portion 13. The preferably rigid attachment of the guide component 10 to the rack 7 assists in ensuring that the second tunnel portion 13, when drilled, will accurately intersect the first tunnel portion 12 without regard to the position of the first tunnel portion 12, forming a functional angled osteal tunnel 4. However, as disclosed in conjunction with FIGS. 16 and 17, in alternate embodiments either or both of the drill guide sleeve 2 and guide component 10 can be slidably mounted on the rack 7.

Referring now to FIG. 3, in an embodiment of a method suitable for use with the present invention, the first tunnel portion 12 is drilled from a first surface 12a of the bone 5 to a predetermined depth into the bone 5. Drilling can be performed free-hand or with a drill guide. Free-hand drilling is performed without the aid of a drill guide, where a first tunnel portion 12 is created by any means known in the art, but preferably using a surgical drill and drill bit 3 or by punching or tamping a tamping plate 19a to create a hole with an awl tip 16a. After a first surface 12a of the bone 5 is chosen, a first tunnel portion can be created by positioning the drill bit 3 over the first surface 12a and engaging the drill. The first tunnel portion 12 is drilled to a predetermined depth, which may be gauged by indicia on the drill or the drill bit 3. The depth of the first tunnel portion 12 is limited to avoid drilling from one surface to an opposing surface of the bone 5.

Referring now to FIG. 4, which shows the surgical tool 8 preferred for use with the present invention in use, after the first tunnel portion 12 is drilled, the guide component 10 is positioned in the first tunnel portion 12, and the drill guide sleeve 2 is placed at the desired position at the second surface 13a of the bone 5. A drill bit 3, sometimes referred to as an osteo drill bit, is aimed by the drill guide sleeve 2 and can be used to drill a measured distance into the bone 5 to create the second tunnel portion 13, which intersects within the interior of the bone 5 at an angle 15 with first tunnel portion 12. The target ring 17 on the interior end 16 of the guide component 10 can be structured to accommodate a drill bit 3 drilling the second tunnel portion 13 through to the first tunnel portion 12. More specifically, and as disclosed in more detail in conjunction with FIG. 15, when the drill bit 3 exits the second tunnel portion 13 and enters the first tunnel portion 12, the drill bit 3 can pass into and through the center of the target ring 17 without touching the guide component 10.

After the first tunnel portion 12 is drilled, the guide component 10 is inserted into the first tunnel portion 12 a certain distance, usually a distance equal or approximately equal to (but not necessarily) the length of the first tunnel portion 12 (see also FIG. 4A). The interior end of guide component 10 is within the bone and generally cannot be seen with the naked eye. The drill guide sleeve 2 then is adjusted on the rack 7 so that the drill guide 2 is located proximal to the position on the second surface 13a of the bone 5 where it is desired to drill the second tunnel portion 13. The positioning of the surgical tool 8 with the guide component 10 within the first tunnel portion 10 and the drill guide sleeve 2 proximal to the surface of the bone 5 where the second tunnel portion 13 is to be drilled allows for a proper drilling location and angle for the second tunnel portion 13. This feature is advantageous because regardless of the relative position or length of the first tunnel portion 12, a user is able to use the surgical tool 8 to achieve any desired entrance or exit point into or out of the bone 5 for the second tunnel portion 13 such that a suture 22 and/or tissue can be threaded into the tunnel and to avoid encountering impediments such as nerves or blood vessels. In other words, the location of the second surface 13a is not dependent upon the location of the first surface 12a and provides a user a great amount of freedom in selecting the entrance and exit points of the angled osteal tunnels 4.

After the drill guide sleeve 2 is positioned at the chosen second surface 13a and clamped into place on the rack 7, the second tunnel portion 13 then is drilled using a drill bit 3 inserted through the drill guide sleeve 2. The rack 7 is structured, and the drill guide sleeve 2 and guide component 10 attached to rack 7, such that the guide sleeve 2 points towards the target ring 17. Thus, the positioning of the drill guide sleeve 2, the guide component 10, and the rack 7 provides for a drilling configuration (that is, not free-hand) whereby the second tunnel portion 13 is drilled at a specific angle 15 and length so as to intersect and connect with the first tunnel portion 12 at a point 14. The drill bit 3 then can be removed from the drill guide sleeve 2. The drill guide sleeve 2 also can be removed from the second tunnel portion 13. In the embodiment disclosed and shown in conjunction with FIGS. 22 and 23, the drill bit 3, 92 and guide wire 94 can be and preferably are left within the second tunnel portion 13 to act as a guide for reamer 90 for enlarging the second tunnel portion 13 (FIG. 23). The target ring 17 now is generally aligned with the axis of the second tunnel portion 13. Alternatively, use of an awl or an awl-tipped guide component 10 or other drilling or tunneling devices and methods can be used.

The guide component 10 and the drill guide sleeve 2 preferably are selectively positionable relative to each other on the rack 7 between the first end and the second end of the rack 7 such that when the interior end of the guide component 10 is located within a first tunnel portion 12 drilled into the bone 5, the drill guide sleeve 2 directs the drill towards the target ring 17, whereby a second tunnel portion 13 drilled into the bone 5 intersects at an angle 15 to the first tunnel portion 12. Preferably, the angle 15 is greater than 0° and less than 180°. More preferably, the angle 15 is between approximately 10° and approximately 170°. The angle 15 also can be between approximately 45° and approximately 135°.

In one embodiment, once the second tunnel portion 13 of the angled osteal tunnel 4 has been completed, the drill bit 3 is removed, and the guide component 10 and the drill guide sleeve 2 can be left in place. Referring now to FIGS. 5 and 6, a suture 22, which may or may not be attached to a torn or synthetic ligament, is fed into the drill guide sleeve 2 and through the second tunnel portion 13. Alternatively, the drill guide sleeve 2 can be removed and the suture 22 fed directly into the second tunnel portion 13. The suture 22 or wire may be fed into the second tunnel portion 13 by any appropriate suture inserter known in the art, including a needle, an alligator clamp, a wire loop, or other known means. The suture 22 is inserted a distance such that the suture 22 interacts with the guide component 10 such that the suture 22 can be seized by the guide component 10. In an embodiment, the suture 22 interacts with the target ring 17 on the interior end 16 of the guide component 10, namely is inserted through the target ring 17, and is seized when a suture clamping component, such as suture seizing pestle 18, in effect clamps the suture 22 against the target ring 17, as disclosed below in conjunction with FIG. 15. Trigger mechanism 21 or scissor handles 40 move the suture seizing pestle 18 into the fixed target ring 17, or alternatively, move the target ring 17 toward the fixed suture seizing pestle 18. The suture 22 seized by the guide component 10 is pulled through and out of the angled osteal tunnel 4 when the guide component 10 is removed from the second tunnel portion 13 while the trigger mechanism 21 or the scissor handles 40 are engaged or squeezed. Such a guide component 10 therefore allows for the intraosseous retrieval of sutures. That is, the suture 22 is within the bone 5, in the angled osteal tunnel 12, 13, and the guide component 10 allows for the retrieving of the suture 22 from within the bone 5 without having to look within the bone 5.

In one illustrative embodiment, the suture seizing mechanism of the guide component 10 is a grip and trigger mechanism 21, wherein the trigger is movable relative to the grip and the trigger is operatively connected to the suture seizing component, such as suture seizing pestle 18, whereby moving the trigger relative to the grip causes the movement of the suture seizing component. In another illustrative embodiment, the suture seizing mechanism is a hinged scissors handle 40 mechanism wherein one scissor handle is movable relative to another scissor handle and one scissor handle is operatively connected to the suture seizing component, such as suture seizing pestle 18, whereby moving the scissor handles relative to each other grip causes the movement of the suture seizing component.

Referring now to FIG. 5, the guide component 10 is left in place in the first tunnel portion 12 and a suture 22 is inserted into the length of the second tunnel portion 13, in a manner and/or using a device as already disclosed, so as to reach the guide component 10 (see FIG. 4). Once inserted into and through the second tunnel portion 13, the suture 22 passes into the target ring 17, which has been left in place in the first tunnel portion 12. Once the first tunnel portion 12 is drilled and the guide component 10 is inserted, the target ring 17 is aligned with the direction of the drill guide sleeve 2 such that both a drill bit 3 and a suture 22 fed into the second tunnel portion 13 through the drill guide sleeve 2 will communicate with and be inserted into the target ring 17 when inserted to the proper depth.

Referring now to FIG. 6, once the suture 22 is inserted to a proper depth so as to enter into the target ring 17, the suture 22 is seized and firmly held by the interaction of the target ring 17 and the suture seizing pestle 18 when the grip 20 and trigger mechanism 21 are engaged by squeezing them together, or alternatively, when the scissor handles 40 are engaged. It should be understood that other preferred embodiments of the suture seizing mechanism may employ other means known in the art to move the suture seizing pestle 18 within the target ring 17 to grasp a suture 22 including electronically-operated mechanisms. With the grip 20 and trigger mechanism 21 in the engaged or squeezed position, the suture 22 is pulled through and out of the first tunnel portion 12 where it can be tied or otherwise secured within the osteal tunnel 4 or outside of the bone 5. For example, one end of the suture 22 can be attached to the ligament or muscle in known manners, and another end of the suture 22 can be attached to the bone 5 in known manners. Alternatively, the attachment methods and means as disclosed in conjunction with FIGS. 10-14 and 19, are preferred.

FIGS. 7, 8, and 9 show illustrative alternatives of a method for drilling or punching osteal tunnels 4 suitable for use in connection with the present invention, including drilling multiple osteal tunnels 4 connected by one intersecting osteal tunnel 4 and drilling multiple angled osteal tunnels 4 emanating from one entrance point at the surface of the bone 5. The disclosed surgical drill guide device allows the user to more easily drill multiple osteal tunnels 4 and multiple intersecting osteal tunnels 12, 13 so as to provide a better anchor for ligaments, tendons and muscle.

Referring now to FIG. 7, an alternate method for drilling angled osteal tunnels 4 suitable for use with the present invention is shown. A first second tunnel portion 25 and a second second tunnel portion 26 can be drilled in a linear configuration. The multiple second tunnel portions 25, 26 intersect and connect with a single first tunnel portion 12. For example, a single first tunnel portion 12 can be drilled or punched freehand as disclosed previously at a desired first surface 12a of the bone. After the first tunnel portion 12 is drilled, the guide component 10 is inserted into the first tunnel portion 12 a certain first distance. The drill guide sleeve 2 then is moved to a desired location at a first second surface 25 of the bone 5 and is adjusted on the rack 7 at the desired first second surface 25a of the bone 5 to allow for a drilling location, angle and distance desired for a first second tunnel portion 25. This first second tunnel portion 25 then is drilled using the drill guide sleeve 2, guide component 10, and rack 7 configuration as disclosed previously so as to intersect and connect with the first tunnel portion 12 at a first intersecting point 4a. The guide component 10 then can be moved axially within the first tunnel portion 12 a certain second distance, different than the first distance. The drill guide sleeve 2 then is moved to a second first surface 26a of the bone 5 and is adjusted on the rack 7 to allow for a drilling location, angle and distance desired for a second second tunnel portion 26. This second second tunnel portion 26 then is drilled using the drill guide sleeve 2, guide component 10, and rack 7 configuration in the same manner as the first second tunnel portion 25 so as to intersect and connect with the first tunnel portion 12 at a second intersecting point 4b. The guide component 10 and the drill guide sleeve 2 then can be moved to drill third and additional second tunnel portions (not shown), all of which can intersect with the first tunnel portion 12 at other intersecting points. Sutures 22 can be inserted into each of the second tunnel portions 13, 25, 26, etc., seized one at a time by the suture seizing mechanism, and pulled through the first tunnel portion 12, to be secured using the methods and devices disclosed herein. The second tunnel portions can be parallel to each other, as shown in FIG. 7, in parallel planes to each other, or at angles to each other, as desired or required by the circumstances.

Referring now to FIG. 8, another alternate method for drilling angled osteal tunnels 4 suitable for use with the present invention is shown. A first second tunnel portion 25, a second second tunnel portion 26, and a third second tunnel portion 27 can be drilled in a fan-shaped configuration, or any geometric configuration relative to the first tunnel portion 12. This method includes drilling a number of second tunnel portions 25, 26, 27, and more if desired, for intersecting with a smaller number of first tunnel portions 12 such that at least one first tunnel portion 12 intersects and connects with at least two second tunnel portions 25, 26, for example. This alternative is similar to the alternative disclosed above, but at least three second tunnel portions 25, 26, 27 are drilled, with at least two of the second tunnel portions, 25, 26, for example, intersecting and connecting with one of the first tunnel portions 12. A third tunnel portion 28 also can be drilled to intersect with one of the second tunnel portions. Various configurations of intersecting first, second, and third tunnel portions are envisioned to enhance the anchoring of the tendons, ligaments or muscles. One limitation to the number of tunnels drilled is, of course, the size and thickness of the bone 5 and the available area with which to work, and the ability to pass sutures through the connecting tunnel portions.

As shown in FIG. 8, third tunnel portion 28 intersects with third second tunnel portion 27 but not with the first tunnel portion 12. As described above, the first tunnel portion 12 is drilled free-hand. The guide component 10 is inserted into the first tunnel portion 12 and the drill guide sleeve 2 is positioned to create third second tunnel portion 27. Then, the guide component 10 is inserted into third second tunnel portion 27 and the drill guide sleeve 2 is positioned to create third tunnel portion 28 which does not intersect first tunnel portion 12. Sutures 22 then can be pulled through the various tunnel portions as described above.

Referring now to FIG. 9, in still another illustrative alternate method for drilling angled osteal tunnels 4, multiple first tunnel portions, 30, 31, 32, are drilled free-hand. The guide component 10 is inserted into first first tunnel portion 30, and the drill guide sleeve 2 is positioned above an entrance point 33 to create a first second tunnel portion 30a. The guide component 10 is next inserted into second first tunnel portion 31, and the drill guide sleeve 2 is again positioned above entrance point 33 to create second second tunnel portion 31a. Similarly, the guide component 10 is inserted into third first tunnel portion 32, and the drill guide sleeve 2 is positioned above entrance point 33 so that third second tunnel portion 32a can be drilled. Thus, all of the second tunnel portions 30a, 31a, 32a exit the bone 5 at the same location 33. This configuration also can be done in reverse, with each of the first tunnel portions having the same entrance point. In this example, first tunnel portions would be shown by reference numerals 30a, 30b, 30c, and second tunnel portions would be shown by reference numerals 30, 31, 32. Using entrance point 33, first first tunnel portion 30a, second first tunnel portion 30b, and third first tunnel portion 30c would all be drilled free-hand from entrance point 33. Guide component 10 is inserted into first first tunnel portion 30a, and the drill guide sleeve 2 is positioned proximal to bone 5 so as to be able to drill first second tunnel portion 30. Guide component 10 then is inserted into second first tunnel portion 30b, and the drill guide sleeve 2 is positioned proximal to bone 5 so as to be able to drill second second tunnel portion 31. Guide component 10 then is inserted into third first tunnel portion 30c, and the drill guide sleeve 2 is positioned proximal to bone 5 so as to be able to drill third second tunnel portion 32. Sutures 22 then can be pulled through the various tunnel portions as described above.

In each of the methods disclosed herein, sutures 22 can be tied together to the ends of other sutures 22 extending out of other osteal tunnels 4, or anchored together with sutures 22 extending out of other osteal tunnels 4 using the anchor 29 (see FIGS. 10-14) and anchoring method disclosed herein. A suture can also be tied off in a "mattress" tying method, by looping a suture around a torn ligament or tendon in a mattress suture pattern, and then pulling the suture, and with it, the tendon, into the tunnel.

Referring now to FIGS. 10-14, an anchor 29 and method for anchoring sutures suitable for use with the present invention is disclosed. In the anchor 29 and anchoring method, an anchor 29 is depressed or deformed about a suture 22 needing to be anchored proximal to a bone 5 to prevent the suture 22 from being pulled back through the bone 5. This anchor 29 eliminates the need for the introduction of an invasive anchoring device into the bone 5 itself, such as a staple, or the elaborate tying of the ends of the sutures 22 in knots or to other anchoring devices lodged within or outside of the bone 5.

Referring now to FIG. 10, at least one suture 22 or a wire extending through an angled osteal tunnel 4 can be secured using an anchor 29, thus avoiding the use of knots or a staple into the bone 5. An illustrative anchor 29 is an oval device through which at least one suture 22 can extend. As shown in FIG. 11, multiple sutures 22 can be threaded through one anchor 29. As shown in FIG. 12, after at least one suture 22 is threaded through the anchor 29, the anchor 29 is then compressed or deformed to anchor 29 the at least one suture 22, using compression and/or friction for example, thus preventing the at least one suture 22 from being pulled back through the osteal tunnel 4. In the multi-tunnel embodiments, as depicted in FIGS. 7, 8, and 9, the multiple sutures 22 all can be passed through a single anchor 29. As shown in FIG. 13, after multiple sutures 22 are pulled through angled osteal tunnels 4, the ends of the sutures 22 are drawn through the anchor 29. As shown in FIG. 14, when the anchor 29 is depressed or deformed about sutures 22, the sutures 22 are prevented from being pulled back into the osteal tunnels 4.

Anchor 29 preferably is manufactured out of a deformable or malleable metal or material, which, after being deformed, resists both further deformation and returning to the original shape. Representative shapes of the anchor 29 include a round or oval ring. Other preferred shapes include a U-shape or other open-ended or self-threading shape. Any other shape known in the art suitable for accommodating a suture 22 within is acceptable. The anchor 29 also can have a curved shape that mimics or is similar to the curve of the surface of a bone 5, such that if the anchor 29 is pulled back against the bone 5 by the sutures 22, the anchor 29 can lie relatively flush against the surface of the bone 5. The anchor 29 can be deformed using pliers, forceps, tweezers, or other means for applying pressure from opposing sides. The anchor 29 is deformed until it tightly grips the suture 22.

In another exemplary alternate embodiment of the suture anchoring method suitable for use with the present invention, a suture 22 is threaded through an anchor 29, and then a tendon, ligament or muscle is also threaded through an anchor 29. The anchor 29 then is depressed or deformed about the suture 22 and tendon, ligament or muscle. The suture 22 may be threaded through an osteal tunnel 4, and the other end of the suture 22 can be anchored on the outside of the bone 5 with another anchor 29. Also, an anchor 29 can be used to join together to the ends of other sutures 22 to increase their length by threading one end through the anchor 29 and then threading the end of another suture 22 into the anchor 29 and deforming or depressing the anchor 29 to secure the ends of the sutures 22.

FIG. 15A illustrates a cross-sectional side view of an illustrative guide component 10 showing an illustrative suture seizing mechanism. The scissor handles 40 are positioned on the exterior end 19 and operate a suture seizing pestle 18 within the guide component 10, preferably within a hollow cylinder or another form suitably-shaped for insertion into an osteal tunnel 11. The suture seizing pestle 18 is within the cylinder when the scissor handles 40 are not squeezed or engaged such that it does not block the opening of the target ring 17. FIG. 15B illustrates a view of an ungripped or untrapped suture 22 within the target ring 17. When engaged, the scissor handles 40 move the suture seizing pestle 18 toward the awl tip 16a of the cylinder and through the opening of the target ring 17, which securely presses the suture seizing pestle 18 against the tip of the cylinder or the edge of the target ring 17 on the interior end 16, thus trapping the suture 22.

FIG. 15C illustrates a view of a gripped or trapped suture 22 within the target ring 17. As a result, the end of a suture 22 fed into an osteal tunnel 11 is directed into the target ring 17, and can be gripped by the suture seizing pestle 18 when the suture 22 is pinched between the suture seizing pestle 18 and the wall, ring, or tip of the interior end 16 when the scissor handles 40 are engaged. This allows the suture 22 to be easily pulled through an angled osteal tunnel 11, and for the tendon 104 to be easily pulled into the enlarged second tunnel portion 13 (see FIG. 24). It should be understood to those skilled in the art that the scissor handles 40 or grip 20 and trigger mechanism 21 used to engage the suture seizing pestle 18 in the target ring 17 are only example embodiments and that any suitable means for engaging the suture seizing pestle 18 can be used.

The target ring 17 is on the interior end 16 of the guide component 10 and, in one embodiment of the surgical tool 8, is a circular or oval hole in cylindrical guide component 10 (FIGS. 2A and 4). The circular or oval void defined by the target ring 17 is suitable for accommodating a typical drill bit 3 so that the drill bit 3 is directed into the void so that the drill bit 3 does not drill into or damage the body of the guide component 10.

In an alternate embodiment, the suture seizing pestle 18 is stationary and fixed to the guide component 10, and the target ring 17 is engaged by squeezing or compressing the grip 20 and trigger mechanism 21 or scissor handles 40 to draw the target ring 17 toward the fixed suture seizing pestle 18 so as to pin the suture 22 against the inner surface of the target ring 17, thus seizing the suture 22. Similarly, as the guide component 10 is removed from the first tunnel portion 12, the suture 22 is pulled through the angled osteal tunnel 11. As shown and disclosed in connection with FIG. 24, the suture 22 can be pulled further so as to draw tendon 104 into reamed second tunnel portion 13.

FIG. 16 illustrates an alternate embodiment of the surgical drill guide device shown in FIG. 2A having a movable guide component 10 and a straight rod 41 and plunger 42 suture seizing mechanism. The guide component 10 is slidably or removably mounted to the rack 7, which may be arcuate in shape, and is capable of being securely positioned about the rack 7 toward either end. The guide component 10 can be fixed into a desired position by engaging clamp 23 with tightening screw 24. In this embodiment, drill guide sleeve 2 remains fixed to an end of the rack 7. In this alternate embodiment, the grip 20 and trigger mechanism 21 is replaced with a straight rod 41 and plunger 42. The straight rod 41 functions as a suture seizing pestle 18 and has one end attached to the plunger 42, and the other end is a free end. The straight rod 41 is slidably received within a cylinder 43 and moves out through the cylinder 43 as the plunger 42 is pulled outward, and moves into the cylinder 43 as the plunger 42 is depressed. A suture 22 is seized within the target ring 17 by squeezing the suture 22 between the target ring 17 and the free end of the straight rod 41 as the plunger 42 is depressed.

FIG. 17 illustrates an alternate embodiment of the surgical drill guide device shown in FIG. 2A having a movable drill guide sleeve 2 and a movable guide component 10. The guide component 10 and the drill guide sleeve 2 are each slidably or removably mounted to the rack 7, which may be arcuate in shape, and are capable of being securely positioned about the rack 7 in a desired position. The guide component 10 and the drill guide sleeve 2 can be fixed in a position on the rack 7 by engaging clamp 23 with tightening screw 24.

FIGS. 18A and 18B are close-up views of the clamp 23 and tightening screw 24. The clamp 23 is attached to an adjustable portion of the surgical drill guide component 10. The adjustable portion preferably is the exterior end 19 of the guide component 10, but alternatively may be the drill guide sleeve 2. Rack 7 is slidably disposed within clamp 23 such that clamp 23 and guide component 10 can be positioned about rack 7. Tightening screw 24 moves clamp 23 toward rack 7 as it is turned one way, fixing clamp 23 and guide component 10 to the rack 7. When turned in an opposite direction, the tightening screw 24 moves the clamp 23 away from the rack 7, making the clamp 23 loose and adjustable.

Referring now to FIG. 19, an alternate method for tying and anchoring a ligament 44 with a suture 22 between osteal tunnels 4 is shown. Using this method, first tunnel portion 12 and second tunnel portion 13 are drilled or punched in the manners described above. A suture 22 or wire is drawn through the osteal tunnels 4, with one free end of the suture 22 extending from the first tunnel portion 12, and one free end of the suture 22 extending from the second tunnel portion 13. The free end of suture 22 extending from the second tunnel portion is wrapped around ligament 44 (or tendon or muscle) and bone 5, such that ligament 44 is sandwiched between suture 22 and bone 5 between the entrance points of the first tunnel portion 12 and the second tunnel portion 13 on the surface of the bone 5. The free end of the suture 22 extending from the second tunnel portion 13 is then tied or anchored using the novel anchor 29 of the present invention to the free end of the suture 22 extending from the first tunnel portion 12. Alternatively, the free end of the suture 22 extending from the first tunnel portion 12 can be drawn over the ligament 44, and the suture can be secured at any point between the entrance points of the first tunnel portion 12 and second tunnel portion 13.

Other methods of fixating the sutures 22 also are contemplated for use with the present invention. For example, one can tie sutures exiting from different tunnels to each other. One can use an interference type of device, such as a plug, placed in the exiting tunnel so as to frictionally engage the suture against the tunnel wall. One can tie the sutures form the exiting tunnel over a button having a larger diameter than the tunnel. Various other known methods for tying sutures also can be utilized.

Referring now to FIG. 20, a suture feeding sleeve 70 for use as a part of the present invention is shown. Suture feeding sleeve 70 is a generally tubular structure 72 having a hollow interior 82, an outer diameter 74 smaller than tunnel portions 12, 13 in general, and smaller than second tunnel portion 13 in particular, and an inner diameter 76 large enough to accommodate a variety of sutures 22. Further, the outer diameter 74 also preferably is larger than the diameter of the opening of target ring 17 to prevent the suture feeding sleeve 70 from entering the target ring 17 when in use, as disclosed in more detail below. Suture feeding sleeve 70 can have a rounded insertion edge 78 for ease of insertion into tunnel portion 12, 13, and a flanged outer edge 80 for ease of gripping and removing.

Referring now to FIG. 21, in one illustrative embodiment, suture feeding sleeve 70 is inserted into either second tunnel portion 13 or first tunnel portion 12 while guide component 10 remains in either first tunnel portion 12 or second tunnel portion 13, respectively. As the outer diameter 74 of suture feeding sleeve is larger than the diameter of the opening of target ring 17, suture feeding sleeve 70 will contact guide component 10, but will not enter target ring 17. Suture 22 then can be fed down through the hollow interior 82 of suture feeding sleeve 70 and into the target ring 17 where suture 22 can be seized, as disclosed above. In another illustrative embodiment, suture 22 can be fed down through the hollow interior 82 of suture feeding sleeve 70 prior to the insertion of the suture feeding sleeve 70 into the tunnel portion 12, 13. In this embodiment, suture 22 can be fed through the hollow interior 82 so as to extend out of the insertion edge 78 a certain desired distance, the distance being chosen to allow just enough of the suture 22 to extend out of the hollow interior 82 so that just enough of suture 22 can extend into target ring 17 and be seized, without having to estimate the amount of suture 22 to be fed into hollow interior 82. Suture feeding sleeve 70 can be appropriately calibrated for such distances.

Referring now to FIGS. 22 and 23, the various osteo tunnels, preferably such as those made by the surgical drill guide device, can be widened or reamed. In one illustrative embodiment, a manual bone reamer 90 is used to enlarge an angled osteal tunnel 4. First tunnel portion 12 can be punched or drilled using methods disclosed herein. Guide component 10 is inserted into the first tunnel portion 12 and drill guide sleeve 2 is positioned over a desired entrance point on the bone 5. A second tunnel portion 13 is drilled with a burr 92 attached to a guide wire 94 such that the first and second tunnel portions 12, 13 intersect. The guide wire 94 is left in the second tunnel portion 13 in the bone while the guide sleeve 2 and the guide component 10 are optionally removed. Burr 92 and guide wire 94 can be a component structure that can be used to drill second tunnel portion 13 and to guide reamer 90. Alternatively, burr 92 and guide wire 94 can be a common drilling set that is removed from the second tunnel portion 13 after drilling and replaced with a different guide wire (not shown) for guiding the reamer 90.

A manual reamer 90, having a shaft 96, handle 98, reaming tip 99, and axial bore 100 extending through reaming tip 99 and shaft 96, is positioned about the guide wire 94 to guide and locate the reamer 90, specifically reaming tip 99, at the entrance to or within the second tunnel portion 13. Specifically, the end of the guide wire 94 extending out of the bone 5 is threaded through the bore 100 such that the reamer 90 can slide over and be guided by the guide wire 94. The handle 98 of the reamer 90 is turned and an appropriate amount of pressure is applied to excavate (ream) an enlarged section 102 within the second tunnel portion 13 to a desired depth. Various reamer 90 configurations can be used, such as various diameters for creating enlarged sections of desired diameters. For example, the reaming tip 99 can be rounded, flat, concave, pointed, or otherwise specially shaped for enlarging second tunnel portion 13 so as to suit the specific needs of the user. Guide wire 94 preferably is relatively rigid, namely rigid enough to provide a suitable guide path for reamer 90. The reamer 90 is constructed of any suitable material known in the art, for example, surgical steel. A rotary power transmission source may also be used in conjunction with the reamer 90 in known manners. The reaming also can be done to first tunnel portion 12 or any other suitable and appropriate tunnel portion(s).

Once the desired geometry of the enlarged section 102 is achieved, the guide component 10 can be re-inserted, if previously removed, into the second tunnel portion 13. A first end of a suture 22 can be tied to a muscle, tendon or ligament in need of repair and the other end of the suture 22 can be fed into the enlarged section 102. The target ring 17 and suture seizing pestle 18, located in the first tunnel portion 12, are used to grip the suture 22 and pull it through the first and second tunnel portions 12, 13, until a desired portion of or the entire muscle, ligament or tendon in need of repair is pulled into the enlarged section 102. FIG. 24 illustrates a tendon 104 attached to muscle 106 pulled into enlarged section 102. Sutures 22 have been tied to tendon 104 and pulled through angled osteal tunnel 12, 13. By pulling sutures 22, tendon 104 is drawn into enlarged section 102. As the bone tissue in and around the enlarged section 102 heals, the muscle 106, ligament 44 or tendon 104 is secured within the bone 5, and the resultant mend often is superior in strength and stability to anchoring the muscle 106, ligament 44 or tendon 104 on the bone using standard anchoring devices and methods.

The technique of tendon reattachment to bone using the present invention also can be exemplified with the technique of arthroscopic biceps tenodesis. In this technique, the biceps is released from the labral rim in the standard fashion, retrieved from the joint and tagged. Using the device and method for drilling angled osteal tunnels disclosed herein, the drill guide 2 is placed over the insertion site in the bicipital groove, and the guide handle laterally on the tuberosity at the site for suture exit. After the first tunnel portion 12 is made and the guide component 10 inserted, the second tunnel portion 13 is drilled. The guide wire 94 is inserted at least 2 cm, and is over-reamed with the reamer 90 for at least 1.5 cm, or ¾ of the way. The guide wire 94 is then removed, an inserter or suture guide utilized, the suture 22 passed, and the sutures 22 from the tagged biceps are pulled through the reamed tunnel 12, 13 and exited laterally, to be fixed with a suture staple or anchor 29.

Thus, in use, the present methods allow for the creation of enlarged osteal tunnels and/or enlarged osteal tunnel sections providing robust bony bridges even with minimal distance between the surface points of entry and exit on the bone. The osteal tunnels and enlarged sections can be created through limited exposure of the muscle, ligaments, tendons, nerves, and bone (i.e., limited exposure of the subdermal structures), and the technique may be performed arthroscopically. For example, arthroscopic surgery of the shoulder to repair a torn rotator cuff involves fixation of the torn tendon to bone. Straight tunnels are precluded because the closer the point of entry and exit, the more shallow the tunnel and the weaker the bony bridge. The present invention addresses this issue.

Further, the present methods allow for the blind intraosseous preparation of enlarged osteal tunnels or tunnel sections and retrieval of sutures, without the need for direct visualization of the tunnels or the sutures. The ability to prepare enlarged osteal tunnels or tunnel sections, to retrieve sutures from within the tunnels without direct visualization, and to draw tissue into the enlarged osteal tunnel can help simplify this type of surgery, reduce surgical errors, and provide for a superior mend.

It is to be understood that the present invention is by no means limited to the particular constructions and method steps herein disclosed or shown in the drawings, but also comprises any modifications or equivalents within the scope of the claims known in the art. It will be appreciated by those skilled in the art that the devices and methods herein disclosed will find utility with respect to multiple bones, joints, and the like.

What is claimed is:

1. A method for drilling an angled osteal tunnel having an enlarged tunnel portion into a bone comprising:
   a) drilling or punching a first tunnel portion into the bone from a first surface location on the bone, the first tunnel portion having an interior end within the bone and inserting a guide component into the first tunnel a predetermined distance wherein an end of the guide component extends to the interior end equal to a length of the first tunnel, the guide component being affixed to a rack and having a target ring for receiving a drill bit at the end which is inserted to the interior end of the first tunnel, the target ring being an opening on the guide component adjacent the end and sized to allow the drill bit to enter;

b) drilling a second tunnel portion having an interior end within the bone with a drilling device into the bone from a second surface location on the bone by inserting a drill bit into a drill guide sleeve attached to the rack, the drill guide sleeve being aligned to guide a drill bit into the opening of the target ring wherein the drill guide sleeve and the guide component are configured such that the drill guide sleeve is angled directly at the target ring at the end of the guide component such that the second tunnel is drilled directly into the end of the guide component and drilling to a depth to pass into the target ring of the guide component as the drill guide sleeve guides the drilling bit to the interior end of the first tunnel portion, whereby the first tunnel portion and the second tunnel portion intersect at their respective interior ends and connect at an angle, resulting in an angled osteal tunnel;

c) removing the drill bit from the second tunnel and inserting a guide wire into the second tunnel through the drill guide sleeve and thereafter removing the drill guide sleeve leaving the guide wire and joining a reamer to the guide wire, whereby the guide wire extends to the intersection of the first and second tunnel portion and the guide wire remains within the second tunnel portion, the reamer having a diameter greater than a diameter of the second tunnel portion, wherein the reamer comprises an axial bore and the axial bore cooperates with the guide wire to guide the reamer along the guide wire;

d) contacting the reamer to the second surface location on the bone; and e) rotating the reamer such that a portion of second tunnel portion is excavated, resulting in an enlarged tunnel section of the second tunnel within the angled osteal tunnel extending from the second surface location partially into the second tunnel.

2. The method as claimed in claim 1, wherein the step of a) drilling or punching the first tunnel portion occurs at the predetermined distance into the bone at a location a suitable distance from a torn tendon or ligament; and the step of b) drilling the second tunnel portion whereby the second tunnel portion is drilled or punched at a specific angle and length so as to intersect and connect with the first tunnel portion, thereby creating the angled osteal tunnel within the bone; and further comprises adjusting the drill guide sleeve on the rack relative to the guide component to allow for a drilling angle and drilling distance desired for drilling the second tunnel portion to the depth to allow the drill bit to enter the end of the guide component into the target ring thereby precisely stopping at the intersection of the first tunnel inside the target ring.

3. The method as claimed in claim 1, wherein the angle is greater than 0° and less than 180°.

4. The method as claimed in claim 1, wherein the angle is between approximately 10° and approximately 170°.

5. The method as claimed in claim 1, wherein the angle is between approximately 45° and approximately 135°.

6. The method as claimed in claim 2, wherein the first tunnel portion is drilled or punched free-hand.

7. The method as claimed in claim 6, wherein the step of punching the first tunnel portion includes free-hand punching an awl tip located on the guide component into the bone.

8. The method as claimed in claim 1, further comprising threading one end of a suture through or about a muscle, tendon or ligament in need of repair.

9. The method as claimed in claim 1, further comprising drilling or punching a plurality of additional second tunnel portions all intersecting and connecting with the first tunnel portion.

10. The method as claimed in claim 9, further comprising excavating at least one of said additional second tunnel portions with a reamer.

11. The method as claimed in claim 1, further comprising drilling or punching a plurality of the second tunnel portions all intersecting and connecting with a plurality of the first tunnel portions, wherein a number of the second tunnel portions are drilled for intersecting with a smaller number of the first tunnel portions such that at least one of the first tunnel portions intersects and connects with at least two of the second tunnel portions, and wherein at least one of said second tunnel portions contains an enlarged section.

12. The method as claimed in claim 1, further comprising drilling or punching a plurality of the first tunnel portions and a plurality of the second tunnel portions, wherein at least one second tunnel portion intersects and connects with each of the first tunnel portions, and wherein at least one second tunnel portion contains an enlarged section.

13. A method for drilling an angled osteal tunnel having an enlarged tunnel portion into a bone comprising:

a) drilling or punching a first tunnel portion into the bone from a first surface location on the bone, the first tunnel portion having an interior end within the bone and inserting a guide component into the first tunnel a predetermined distance wherein an end of the guide component extends to the interior end equal to a length of the first tunnel, the guide component being affixed to a rack and having a target ring for receiving a drill bit at the end which is inserted to the interior end of the first tunnel, the target ring being an opening on the guide component adjacent the end and sized to allow the drill bit to enter;

b) drilling a second tunnel portion having an interior end within the bone with a drilling device into the bone from a second surface location on the bone by inserting a drill bit into a drill guide sleeve attached to the rack, the drill guide sleeve being aligned to guide a drill bit into the opening of the target ring wherein the drill guide sleeve and the guide component are configured such that the drill guide sleeve is angled directly at the target ring at the end of the guide component such that the second tunnel is drilled directly into the end of the guide component and drilling to a depth into the target ring of the guide component as the drill guide sleeve guides the drilling bit to the interior end of the first tunnel portion, whereby the first tunnel portion and the second tunnel portion intersect at their respective interior ends and connect at an angle, resulting in an angled osteal tunnel;

c) removing the drill bit from the second tunnel and inserting a guide wire into the second tunnel through the drill guide sleeve and thereafter removing the drill guide sleeve leaving the guide wire and joining a reamer to the guide wire, whereby the guide wire extends to the intersection of the first and second tunnel portion and the guide wire remains within the second tunnel portion, the reamer having a diameter greater than a diameter of the second tunnel portion, wherein the reamer comprises an axial bore and the axial bore cooperates with the guide wire to guide the reamer along the guide wire;

d) contacting the reamer to the second surface location on the bone;

e) rotating the reamer such that a portion of second tunnel portion is excavated, resulting in an enlarged tunnel section of the second tunnel within the angled osteal tunnel extending from the second surface location partially into the second tunnel; and inserting a suture into the second tunnel portion, and seizing the suture through the first tunnel portion with a suture seizing mechanism integrally formed within said guide component, whereby the suture passes into said target ring and is seized inside the guide component and can be pulled through the first tunnel portion as the guide component is removed from the first tunnel.

14. The method as claimed in claim 13, further comprising the step of attaching an end of the suture to a muscle, ligament or tendon in need of repair.

15. The method as claimed in claim 14, further comprising the step of pulling a portion of a muscle, tendon or ligament in need of repair and the suture into the enlarged tunnel section within the bone, whereby the bone of the enlarged tunnel section heals and reforms over the muscle, tendon or ligament in need of repair.

16. The method as claimed in claim 1, further comprising the steps of
 (f) attaching an end of a suture to a muscle, ligament or tendon in need of repair;
 (g) threading another end of the suture through the angled osteal tunnel; and
 (h) pulling the suture through the angled osteal tunnel thereby pulling a portion of the muscle, tendon or ligament into the enlarged tunnel section whereby the bone of the enlarged tunnel section heals and reforms over the muscle, tendon or ligament.

* * * * *